US010450261B2

(12) United States Patent
Schaub et al.

(10) Patent No.: US 10,450,261 B2
(45) Date of Patent: Oct. 22, 2019

(54) METHOD FOR THE HOMOGENEOUS CATALYTIC REDUCTIVE AMINATION OF CARBONYL COMPOUNDS

(71) Applicant: BASF SE, Ludwigshafen (DE)

(72) Inventors: Thomas Schaub, Neustadt (DE); Joan Gallardo Donaire, Tarragona (ES); Martin Ernst, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/577,393

(22) PCT Filed: May 27, 2016

(86) PCT No.: PCT/EP2016/061999
§ 371 (c)(1),
(2) Date: Mar. 16, 2018

(87) PCT Pub. No.: WO2016/189129
PCT Pub. Date: Dec. 1, 2016

(65) Prior Publication Data
US 2018/0186725 A1 Jul. 5, 2018

(30) Foreign Application Priority Data
May 28, 2015 (EP) .................... 15169539

(51) Int. Cl.
| C07C 209/26 | (2006.01) |
| B01J 31/18 | (2006.01) |
| B01J 31/20 | (2006.01) |
| B01J 31/24 | (2006.01) |
| C07C 213/02 | (2006.01) |
| C07F 17/02 | (2006.01) |
| B01J 31/22 | (2006.01) |
| C07D 265/30 | (2006.01) |
| C07D 317/58 | (2006.01) |

(52) U.S. Cl.
CPC ........... *C07C 209/26* (2013.01); *B01J 31/185* (2013.01); *B01J 31/20* (2013.01); *B01J 31/2295* (2013.01); *B01J 31/2409* (2013.01); *B01J 31/2414* (2013.01); *B01J 31/2433* (2013.01); *C07C 213/02* (2013.01); *C07D 265/30* (2013.01); *C07D 317/58* (2013.01); *C07F 17/02* (2013.01); *B01J 2231/4283* (2013.01); *B01J 2231/44* (2013.01); *B01J 2231/643* (2013.01); *B01J 2531/821* (2013.01); *C07B 2200/07* (2013.01); *C07C 2602/08* (2017.05)

(58) Field of Classification Search
CPC .................................................. C07C 209/26
See application file for complete search history.

(56) References Cited

U.S. PATENT DOCUMENTS

| 6,884,887 B1* | 4/2005 | Riermeier ............ B01J 31/1875 |
| | | 544/106 |
| 7,230,134 B2 | 6/2007 | Borner et al. |
| 2004/0267051 A1* | 12/2004 | Boerner ................ C07C 209/28 |
| | | 564/398 |
| 2016/0264691 A1 | 9/2016 | Maitro-Vogel et al. |
| 2017/0175267 A1 | 6/2017 | Strautmann et al. |
| 2017/0233865 A1 | 8/2017 | Strautmann et al. |
| 2017/0355642 A1 | 12/2017 | Ernst et al. |

FOREIGN PATENT DOCUMENTS

WO    WO-2007104359 A1    9/2007

OTHER PUBLICATIONS

Breuer et al., "Industrial Methods for the Production of Optically Active Intermediates", *Angew. Chem. Int. Ed..*, vol. 43, pp. 788-824 (2004).
Ghislieri et al., "Biocatalytic Approaches to the Syntheseis of Enantiomerically Pure Chiral Amines", *Top Catal*, vol. 57, pp. 284-300 (2014).
Gunanathan et al., "Selective Synthesis of Primary Amines Directly from Alcohols and Ammonia", *Angew. Chem. Int. Ed.*, vol. 47, pp. 8661-8664 (2008).
Nugent, "Asymmetric Reductiive Amination", *Chiral Amine Synthesis: Methods, Developments and Applications*, pp. 225-245 (2010).
Pingen et al., "Mechanistic Study on the Ruthenium-Catalyzed Direct Amination of Alcohols", *Organometallics*, vol. 33, pp. 1623-1629, (2014).
Talwar et al., "Primary Amines by Transfer Hydrogenative Reductive Amination of Ketones by Using Cyclometalated $Ir^{III}$ Catalysts", *Chem. Eur. J.*, vol. 20, pp. 245-252 (2014).
International Search Report for PCT/EP2016/061999 dated Jul. 26, 2016.
Written Opinion of the International Searching Authority for PCT/EP2016/061999 dated Jul. 26, 2016 (in German).

* cited by examiner

*Primary Examiner* — Paul V Ward
(74) *Attorney, Agent, or Firm* — Drinker Biddle & Reath LLP

(57) ABSTRACT

The present invention relates to a method for the reductive amination of a carbonyl compound, comprising one or more carbonyl groups amenable to reductive amination, forming the corresponding primary amine, characterized in that the reaction is carried out in the presence of a homogeneously dissolved catalyst complex K, comprising at least one metal atom from Group 8, 9 or 10 of the periodic table, bearing a bidentate phosphane ligand, a carbonyl ligand, a neutral ligand and a hydride ligand, and also an acid as co-catalyst.

16 Claims, No Drawings

METHOD FOR THE HOMOGENEOUS CATALYTIC REDUCTIVE AMINATION OF CARBONYL COMPOUNDS

CROSS-REFERENCE TO RELATED APPLICATIONS

This application is a national stage application (under 35 U.S.C. § 371) of PCT/EP2016/061999, filed May 27, 2016, which claims benefit of European Application No. 15169539.2, filed May 28, 2015, both of which are incorporated herein by reference in their entirety.

The present invention relates to a method for the reductive amination of a carbonyl compound, comprising one or more carbonyl groups amenable to reductive amination, forming the corresponding primary amine, wherein the reaction is carried out in the presence of a homogeneously dissolved catalyst complex K, comprising at least one metal atom from Group 8, 9 or 10 of the periodic table, bearing a bidentate phosphane ligand, a carbonyl ligand, a neutral ligand and a hydride ligand, and also an acid as co-catalyst.

BACKGROUND OF THE INVENTION

Primary amines are used as versatile intermediates, for example, for preparing pharmaceuticals or agrochemicals (Amines, Aliphatic, *Ullmann's Encyclopedia of Industrial Chemistry*, 2012, Vol. 2, pp. 647-695). Enantiomerically pure, chiral amines in particular are valuable building blocks in this connection.

Primary amines may be prepared in various ways, although the reductive amination of carbonyl compounds with ammonia and hydrogen is a particularly atom-efficient method, since no further co-products arise apart from water.

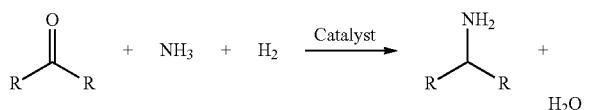

On an industrial scale, heterogeneous catalysts are mostly used for this purpose, although with these systems, however, enantiomerically pure chiral amines cannot be obtained. Commercially, primary, enantiomerically pure chiral amines are usually prepared from the racemic mixtures of the corresponding amines via multistage enzymatic methods (D. Ghislieri, N. J. Turner, *Top. Catal.* 2014, 57, 284-300; *Angew. Chem. Int. Ed.* 2004, 43, 788-824).

A direct method for preparing primary amines is homogeneously catalyzed reductive amination, which may also be conducted asymmetrically for the synthesis of enantiomerically pure chiral amines (Thomas C. Nugent (Ed.), *Chiral Amine Synthesis*, 2010, pp. 225-245, Wiley-VCH, Weinheim).

U.S. Pat. No. 6,884,887 discloses the reductive amination of carbonyl compounds with amines and hydrogen using homogeneously dissolved transition metal phosphane complexes. When using ammonia for preparing primary amines using the rhodium and iridium catalysts described, which bear bidentate phosphane ligands, unsatisfactory selectivities at high rates of conversion are obtained under these conditions, however, due to the undesired hydrogenation of the carbonyl compound to the corresponding alcohol. The highest amine:alcohol selectivities described here, in the case of complete conversion of the carbonyl compound, are 4:1, i.e. 20% of the undesired alcohol is formed as by-product in the system described. For the amination with $NH_3$ in this case, no catalysts bearing a carbonyl ligand were used and no acid as co-catalyst was added. The asymmetric amination with ammonia with the catalysts claimed is also not substantiated by examples. A disadvantage of this system is the formation of relatively large amounts of alcohols as undesired by-products.

US2004/0267051 discloses the reductive amination of carbonyl compounds with amines using homogeneously dissolved transition metal phosphane complexes, in which not hydrogen but hydrogen donors such as ammonium formate from a transfer hydrogenation are used. According to US2004/0267051, a distinctly higher selectivity is achieved with respect to the amine (no formation of alcohol at conversions of up to 96% of the carbonyl compound) by transfer hydrogenation using comparable transition metal catalysts, as described in U.S. Pat. No. 6,687,887, than by using hydrogen as reducing agent. According to US2004/0267051, the amines may also additionally be prepared enantioselectively using chiral phosphane ligands. A disadvantage of this method is that very inexpensive hydrogen cannot be used as reducing agent in order to achieve high selectivities but significantly more expensive reducing agents have to be used for a transfer hydrogenation.

It is likewise proposed in Chem. Eur. J. 2014, 20, 245-252 that the reductive amination of ketones to primary amines is carried out using ammonium formate as reducing agent and $NH_3$ source in order to achieve the highest possible selectivities of the desired amine and to suppress the formation of alcohols. In this case, homogeneously dissolved half-sandwich iridium complexes are used as catalysts. Similarly disadvantageous is that inexpensive hydrogen cannot be used as reducing agent and in addition formamides of the products are also formed as by-products, which are only converted to the desired amine by a downstream hydrolysis.

The object, therefore, consisted of providing a method by which the disadvantages discussed above can be avoided. Such a method should be simple to carry out, be carried out using ammonia as amine source and hydrogen as reducing agent and afford as little as possible of the undesired alcohols as by-product. In addition, it should also be possible using this method to prepare the amines enantioselectively.

SUMMARY OF THE INVENTION

The above object for preparing primary amines could be achieved, surprisingly, by using specific metal catalysts for homogeneously catalyzed reductive amination.

DETAILED DESCRIPTION OF THE INVENTION a) General Definitions

In the absence of any other statements, the following general definitions apply according to the invention:

"Homogeneously catalyzed" is understood in the context of the present invention to mean that the catalytically-active part of the catalyst complex is present at least partly dissolved in the liquid reaction medium. In a preferred embodiment, at least 90% of the catalyst complex used in the method is present dissolved in the liquid reaction medium, more preferably at least 95%, particularly preferably more than 99%, the catalyst complex most preferably being present completely dissolved in the liquid reaction medium (100%), based in each case on the total amount in the liquid reaction medium. The amount of catalyst is generally 0.1 to 5.000 ppm by weight, based in each case on the total liquid reaction medium.

"Stereoisomers" are compounds of identical constitution but different atom arrangements in three-dimensional space.

"Enantiomers" are stereoisomers which behave as mirror images to one another. The "enantiomeric excess" (ee) achieved in an asymmetric synthesis is given by the following formula:

$$ee[\%]=(R-S)/(R+S)\times 100.$$

R and S are the descriptors of the CIP system for the two enantiomers and reflect the absolute configuration at the asymmetric atom. The enantiomerically pure compound (ee=100%) is also referred to as a "homochiral compound".

b) Definitions of Chemical Residues
b1) Aliphatic Non-cyclic Residues

Unless otherwise defined, the term "alkyl" is to be generally understood in broad terms. In particular, "alkyl" in the broadest sense comprises aliphatic, straight-chain or branched, non-cyclic hydrocarbon residues having 1 to 30 carbon atoms, which optionally in addition may comprise in its chain one or more, e.g. 1, 2 or 3 heteroatoms such as O, N, NH or S. "Alkyl", which optionally in addition may comprise in its chain one or more, e.g. 1, 2 or 3 heteroatoms such as O, N, NH or S. "Alkyl" residues in the broadest sense may also be mono- or polyunsaturated and may have one or more, e.g. 1 to 5, such as 1, 2 or 3, non-cumulative C—C double bonds or C—C triple bonds, in particular 1, 2 or 3 double bonds. They may be of natural or synthetic origin. The expression "alkyl" also comprises substituted alkyl groups which may generally bear 1, 2, 3, 4 or 5, preferably 1, 2 or 3 and particularly preferably 1 substituent(s). The abovementioned residues can also be summarized under the generic term "hydrocarbyl" residues.

These "substituents" are particularly selected from F, Cl, Br, hydroxyl (OH), $C_1$-$C_{30}$-alkoxy, $C_5$-$C_{30}$-aryloxy, $C_5$-$C_{30}$-alkylaryloxy, $C_5$-$C_{30}$-heteroaryloxy comprising at least one heteroatom selected from N, O, S or oxo, $C_3$-$C_{30}$-cycloalkyl, phenyl, $C_5$-$C_{30}$-heteroaryl comprising at least one heteroatom selected from N, O or S, $C_5$-$C_{30}$-heterocyclyl comprising at least one heteroatom selected from N, O, S, naphthyl or amino, $C_1$-$C_{30}$-alkylamino, $C_5$-$C_{30}$-arylamino, $C_5$-$C_{30}$-heteroarylamino comprising at least one heteroatom selected from N, O or S, $C_1$-$C_{30}$-dialkylamino, $C_5$-$C_{14}$-diarylamino, $C_6$-$C_{20}$-alkylarylamino, $C_1$-$C_{30}$-acyl, $C_1$-$C_{30}$-acyloxy, $NO_2$, $C_1$-$C_{30}$-carboxyl, carbamoyl, carboxamide, cyano, sulfonyl, sulfonylamino, sulfinyl, sulfinylamino, thiol, $C_1$-$C_{30}$-alkylthiol, $C_5$-$C_{30}$-arylthiol and $C_1$-$C_{30}$-alkylsulfonyl ("Group 1 substituents").

Non-limiting examples of the abovementioned "alkyl" ("hydrocarbyl") groups according to the invention to be mentioned according to the above general definition are:

"Alkyl" in a narrow sense (and also all alkyl groups in residues derived therefrom such as alkoxy, alkylthio, alkoxyalkyl, alkoxyalkoxy, hydroxyalkyl, aminoalkyl, alkylamino and dialkylamino; haloalkyl, aralkyl and also acyl or alkoxycarbonyl) specifically represents saturated, straight-chain or branched hydrocarbon residues, not comprising any heteroatoms, having 1 to 4, 1 to 5, 1 to 6, or 1 to 7, 1 to 10, 1 to 20 or 1 to 30 carbon atoms, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; and also n-heptyl, and the singly or multiply branched analogs thereof. Octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, squalyl, constitutional isomers, particularly singly or multiply branched isomers and higher homologs thereof.

"Heteroalkyl" in particular represents specific alkyl residues listed in the group above which additionally may comprise in their chain one or more, e.g. 1, 2 or 3 heteroatoms, such as O, N, NH, S.

"Lower alkyl" represents alkyl residues above having 1 to 4, 1 to 5, 1 to 6, or 1 to 7 carbon atoms.

"Alkenyl" comprises mono- or polyunsaturated, particularly monounsaturated analogs of the above alkyl groups and at least one C—C double bond. In particular, the term comprises mono- or polyunsaturated, particularly monounsaturated, straight-chain or branched hydrocarbon residues having 2 to 4, 2 to 6, 2 to 8, 2 to 10, 2 to 20 or 2 to 30 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl,3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" comprises mono- or polyunsaturated, particularly monounsaturated analogs of the above alkyl groups and at least one C—C triple bond. In particular, the term comprises mono- or polyunsaturated, particularly monounsaturated, straight-chain or branched hydrocarbon residues having 2 to 4, 2 to 6, or 2 to 8 carbon atoms and a triple bond in any position, particularly residues having a C—C triple bond analogous to the alkenyl residues explicitly mentioned above; e.g. $C_2$-$C_6$-alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 3-methyl-1-butynyl, 1-methyl-2-butynyl, 1-methyl-2-butynyl, 1-methyl-3-butynyl, 2-methyl-3-butynyl, 1,1-dimethyl-2-propynyl, 1-ethyl-2-propynyl, 1-hexynyl and isomeric forms thereof.

"Haloalkyl" comprises straight-chain or branched alkyl groups having 1 to 4, 1 to 6, 1 to 8, 1 to 10 or 1 to 20 carbon atoms (as previously mentioned), wherein the hydrogen atoms in these groups may be partially or completely replaced by halogen atoms as previously mentioned, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

"Hydroxyalkyl" represents especially the mono- or polyhydroxylated, especially monohydroxylated, analogs of the above alkyl residues, for example the monohydroxylated analogs of the above straight-chain or branched alkyl residues, for example the linear hydroxyalkyl groups, such as those having a primary (terminal) hydroxyl group, such as hydroxymethyl, 2-hydroxyethyl, 3-hydroxypropyl, 4-hydroxybutyl, or those having nonterminal hydroxyl groups, such as 1-hydroxyethyl, 1- or 2-hydroxypropyl, 1- or 2-hydroxybutyl or 1-, 2- or 3-hydroxybutyl.

"Hydroxyalkenyl" represents especially the mono- or polyhydroxylated, especially monohydroxylated, analogs of the above alkenyl residues.

"Aminoalkyl" and "aminoalkenyl" represent especially the mono- or polyaminated, especially monoaminated, analogs of the above alkyl and alkenyl residues respectively, or analogs of the above hydroxyalkyl where the OH group has been replaced by an amino group.

"Alkoxy" represents especially the oxygen-terminated analogs of the above alkyl residues. Non-limiting examples include: $C_1$-$C_6$-alkoxy residues such as methoxy, ethoxy, n-propoxy, 1-methylethoxy, butoxy, 1-methylpropoxy, 2-methylpropoxy or 1,1-dimethylethoxy, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

"Alkoxyalkyl" represents especially the above alkyl groups bearing at least one of the alkoxy residues mentioned above as substituents.

"Alkoxycarbonyl" represents especially the above alkyl groups bonded to a carbonyl group.

"Alkylthio" represents especially the S-terminated analogs of the above alkoxy residues.

"Haloalkoxy" represents an alkoxy residue having 1 to 8, particularly 1 to 6 and especially 1 to 4 carbon atoms, as mentioned previously, which has been partially or completely substituted by fluorine, chlorine, bromine and/or iodine, preferably by fluorine, i.e. for example $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

b2) Polymeric Residues

"Polyalkylene" residues comprise in particular those which are formed essentially from $C_{2-6}$, especially $C_{2-4}$, monomer units, such as ethylene, propylene, n- or isobutylene or mixtures thereof and have a degree of polymerization of 2 to 100, or 3 to 50 or 4 to 25 or 5 to 10.

"Polyalkylene oxide" represents in particular a residue derived from the same or different $C_{2-4}$-oxyalkylene monomer units having a degree of polymerization of 2 to 100, or 3 to 50 or 4 to 25 or 5 to 10.

"Polyalkylenimine" represents the structural analog residues of the above polyalkylene oxide residues, where the oxygen atom has been replaced by imine groups.

b3) Acyclic Bridging Groups

"Alkylene" represents straight-chain or singly or multiply branched alkanediyl groups, i.e. hydrocarbon bridging groups having 1 to 10 carbon atoms, for example $C_1$-$C_7$-alkylene groups selected from —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$—, $(CH_2)_4$—, —$(CH_2)_5$—, —$(CH_2)_6$, —$(CH_2)_7$—, —$CH(CH_3)$—$CH_2$—$CH_2$—$CH$ ($CH_3$)— or —$CH(CH_3)$—$CH_2$—$CH_2$—$CH_2$—$CH(CH_3)$— or $C_1$-$C_4$-alkylene groups selected from —$CH_2$—, —$(CH_2)_2$—, —$(CH_2)_3$—, —$(CH_2)_4$—, —$(CH_2)_2$—$CH$ ($CH_3$)—, —$CH_2$—$CH(CH_3)$—$CH_2$— or $C_2$-$C_6$-alkylene groups, for example —$CH_2$—$CH(CH_3)$—, —$CH(CH_3)$—$CH_2$—, —$CH(CH_3)$—$CH(CH_3)$—, —$C(CH_3)_2$—$CH_2$—, —$CH_2$—$C(CH_3)_2$—, —$C(CH_3)_2$—$CH(CH_3)$—, —$CH(CH_3)$—$C(CH_3)_2$—, —$CH_2$—$CH(Et)$-, —$CH(CH_2CH_3)$—$CH_2$—, —$CH$ ($CH_2CH_3$)—$CH(CH_2CH_3)$—, —$C(CH_2CH_3)_2$—$CH_2$—, —$CH_2$—$C(CH_2CH_3)_2$—, —$CH_2$—$CH(n$-propyl)-, —$CH(n$-propyl)-$CH_2$—, —$CH(n$-propyl)-$CH(CH_3)$—, —$CH_2$—$CH$ (n-butyl)-, —$CH(n$-butyl)-$CH_2$—, —$CH(CH_3)$—$CH$ ($CH_2CH_3$)—, —$CH(CH_3)$—$CH(n$-propyl)-, —$CH$ ($CH_2CH_3$)—$CH(CH_3)$—, —$CH(CH_3)$—$CH(CH_2CH_3)$—, or $C_2$-$C_4$-alkylene groups, for example selected from —$(CH_2)_2$—, —$CH_2$—$CH(CH_3)$—, —$CH(CH_3)$—$CH_2$—, —$CH(CH_3)$—$CH(CH_3)$—, —$C(CH_3)_2$—$CH_2$—, —$CH_2$—$C(CH_3)_2$—, —$CH_2$—$CH(CH_2CH_3)$—, —$CH(CH_2CH_3)$—$CH_2$—.

"Oxyalkylene" residues correspond to the definition of the above straight-chain or singly or multiply branched alkylene residues having 2 to 10 carbon atoms, where the carbon chain is interrupted once or more than once, especially once, by an oxygen heteroatom. Nonlimiting examples include: —$CH_2$—O—$CH_2$—, —$(CH_2)_2$—O—$(CH_2)_2$—, —$(CH_2)_3$—O—$(CH_2)_3$—, or —$CH_2$—O—$(CH_2)_2$—, —$(CH_2)_2$—O—$(CH_2)_3$—, —$CH_2$—O—$(CH_2)_3$.

"Aminoalkylene" corresponds to the definition of the above straight-chain or singly or multiply branched alkylene residues having 2 to 10 carbon atoms, where the carbon chain is interrupted once or more than once, especially once, by a nitrogen group (especially —NH— group). Nonlimiting examples include: —$CH_2$—NH—$CH_2$—, —$(CH_2)_2$—NH—$(CH_2)_2$—, —$(CH_2)_3$—NH—$(CH_2)_3$—, or —$CH_2$—NH—$(CH_2)_2$—, —$(CH_2)_2$—NH—$(CH_2)_3$—, —$CH_2$—NH—$(CH_2)_3$.

"Alkenylene" represents the mono- or polyunsaturated, especially monounsaturated, analogs of the above alkylene groups having 2 to 10 carbon atoms, especially $C_2$-$C_7$-alkenylenes or $C_2$-$C_4$-alkenylene, such as —CH=CH—, —CH=CH—$CH_2$—, —$CH_2$—CH=CH—, —CH=CH—$CH_2$—$CH_2$—, —$CH_2$—CH=CH—$CH_2$—, —$CH_2$—$CH_2$—CH=CH—, —$CH(CH_3)$—CH=CH—, —$CH_2$—C ($CH_3$)=CH—. In the case of a substitution, these may bear generally 1, 2, 3, 4 or 5, preferably 1, 2 or 3 and particularly preferably 1 "substituent(s)" according to the above definition, particularly selected from alkyl, aryl, alkoxy and halogen.

b4) Cyclic Residues

"Cycloalkyl" represents carbocyclic, mono- or polycyclic, for example, mono-, bi- or tricylic residues having 3 to 30 or 3 to 20 carbon atoms, for example $C_3$-$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl, cycloheptyl, and also to cyclopropylmethyl, cyclopropylethyl, cyclobutylmethyl, cyclobutylethyl, cyclopentylmethyl, cyclopentylethyl, cyclohexylmethyl, or $C_3$-$C_7$-cycloalkyl such as cyclopropyl, cyclobutyl, cyclopentyl, cyclohexyl, cycloheptyl, cyclopropylmethyl, cyclopropylethyl, cyclobutylmethyl, cyclopentylethyl, cyclohexylmethyl, where the bond to the rest of the molecule may be via any suitable carbon atom. In the case of a substitution, these may bear generally 1, 2, 3, 4 or 5, preferably 1, 2 or 3 and particularly preferably 1 "substituent(s)" according to the above definition, particularly selected from alkyl, aryl, alkoxy and halogen.

"Cycloalkoxy" represents especially the oxygen-terminated analogs of the above cycloalkyl residues.

"Cycloalkenyl" represents mono- or polyunsaturated analogs of the above "cycloalkyl" residues. It represents in particular monocyclic, mono- or polyunsaturated hydrocarbon groups having 5 to 8, preferably to 6, carbon ring members, for example the monounsaturated residues cyclopenten-1-yl, cyclopenten-3-yl, cyclohexen-1-yl, cyclohexen-3-yl and cyclohexen-4-yl. In the case of a substitution, these may bear generally 1, 2, 3, 4 or 5, preferably 1, 2 or 3 and particularly preferably 1 "substituent(s)" according to the above definition, particularly selected from alkyl, aryl, alkoxy and halogen.

"Cycloalkylene" represents especially bridging groups derived from the above cycloalkyl groups, where the bond to the rest of the molecule may be via any suitable carbon atom. In the case of a substitution, these may bear generally 1, 2, 3, 4 or 5, preferably 1, 2 or 3 and particularly preferably 1 "substituent(s)" according to the above definition, particularly selected from alkyl, aryl, alkoxy and halogen.

"Cycloalkenylene" represents especially bridging groups derived from the above cycloalkenyl groups, where the bond to the rest of the molecule may be via any suitable carbon atom. In the case of a substitution, these may bear generally 1, 2, 3, 4 or 5, preferably 1, 2 or 3 and particularly preferably 1 "substituent(s)" according to the above definition, particularly selected from alkyl, aryl, alkoxy and halogen.

"Aryl" according to the invention represents mono- or polycyclic, preferably mono-, bi-, tri- or tetracycylic, optionally substituted aromatic residues having 5 to 20, for example 5 to 10, 5 to 14 or 5 to 18 ring carbon atoms, for example phenyl, tolyl, xylyl, mesityl, biphenyl, naphthyl such as 1- or 2-naphthyl, tetrahydronaphthyl, fluorenyl, indenyl, naphthacenyl and phenanthrenyl. These aryl residues may optionally bear 1, 2, 3, 4, 5 or 6, preferably 1, 2 or 3 and particularly preferably 1 identical or different substituent(s). In the case of a polycyclic aryl residue, at least one of the rings has aromatic character, but more than one or all rings may also have aromatic character.

"Arylalkyl" or "aralkyl" represent the aryl-substituted analogs of the above alkyl residues, where aryl likewise has the definitions stated above, such as phenyl-$C_1$-$C_4$-alkyl residues selected from phenylmethyl or phenylethyl.

"Aryloxy" represents the oxygen-linked analogs of the above optionally substituted aryl residues.

"Substituents" for "aryl"-containing residues specified herein are, in particular, unless indicated otherwise, selected from keto, carboxyl, carboxylate, —COO-alkyl, —OH, —SH, —CN, amino, —$NO_2$, —$SO_3H$, sulfonate, -$NE^1E^2$, -alkylene-$NE^1E^2$, halogen, alkoxy, trifluoromethyl, alkyl or alkenyl groups ("Group 2 substituents").

"Heterocyclyl" comprises groups having 1 to 30 or 2 to 20 or 5 to 12 ring carbon atoms and at least one five- to seven-membered, saturated, partially unsaturated or aromatic heterocycle or heterocyclyl residues comprising one, two, three or four heteroatoms from the group of O, N or S. In the case that nitrogen is a ring atom, the present invention also comprises N-oxides of the nitrogen-containing heterocycles. The following subgroups, for example, may be mentioned:

5- or 6-membered saturated or monounsaturated heterocyclyl, comprising one to two nitrogen atoms and/or an oxygen or sulfur atom or one or two oxygen and/or sulfur atoms as ring members, e.g. 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;

5-membered aromatic heterocyclyl (=heteroaryl or hetaryl), comprising, in addition to carbon atoms, one, two or three nitrogen atoms or one or two nitrogen atoms and one sulfur or oxygen atom as ring members, e.g. 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl and 1,3,4-triazol-2-yl;

5-membered aromatic heterocyclyl (=heteroaryl or hetaryl) having 1, 2, 3 or 4 nitrogen atoms as ring members, such as 1-, 2- or 3-pyrrolyl, 1-, 3- or 4-pyrazolyl, 1-, 2- or 4-imidazolyl, 1,2,3-[1H]-triazol-1-yl, 1,2,3-[2H]-triazol-2-yl, 1,2,3-[1H]-triazol-4-yl, 1,2,3-[1H]-triazol-5-yl, 1,2,3-[2H]-triazol-4-yl, 1,2,4-[1H]-triazol-1-yl, 1,2,4-[1H]-triazol-3-yl, 1,2,4-[1H]-triazol-5-yl, 1,2,4-[4H]-triazol-4-yl, 1,2,4-[4H]-triazol-3-yl, [1H]-tetrazol-1-yl, [1H]-tetrazol-5-yl, [2H]-tetrazol-2-yl and [2H]-tetrazol-5-yl;

5-membered aromatic heterocyclyl (=heteroaryl or hetaryl) having 1 heteroatom selected from oxygen and sulfur and optionally 1, 2 or 3 nitrogen atoms as ring members, for example, 2-furyl, 3-furyl, 2-thienyl, 3-thienyl, 3- or 4-isoxazolyl, 3- or 4-isothiazolyl, 2-, 4- or 5-oxazolyl, 2-, 4- or 5-thiazolyl, 1,2,4-thiadiazol-3-yl, 1,2,4-thiadiazol-5-yl, 1,3,4-thiadiazol-2-yl, 1,2,4-oxadiazol-3-yl, 1,2,4-oxadiazol-5-yl and 1,3,4-oxadiazol-2-yl;

6-membered heterocyclyl (=heteroaryl or hetaryl), comprising, in addition to carbon atoms, one or two or one, two or three nitrogen atoms as ring members, e.g.

2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl; 1,2,4-triazin-5-yl, 1,2,4-triazin-6-yl and 1,3,5-triazin-2-yl.

"Heterocyclyl" also in particular comprises "polycyclic", for example bicyclic or tricyclic, ring systems, in which one of the abovementioned monocyclic heterocylcyl residues is condensed with at least one further, identical or different heterocycle, at least one aryl ring and/or at least one cycloalkyl or cycloalkenyl ring according to the above definition in each case.

"Heteroaryl" also in particular comprises "polycyclic", for example bicyclic or tricyclic, ring systems, in which one of the abovementioned monocyclic heteroaryl residues is condensed with at least one further, identical or different heteroaryl ring, at least one aryl ring and/or at least one cycloalkyl or cycloalkenyl ring according to the above definition in each case.

The above "heterocyclyl" or heteroaryl groups may be unsubstituted or substituted with one or more, e.g. 1, 2, 3, 4 or 5, particularly 1, 2 or 3 substituents of the "Group 1 substituents".

A preferred sub-group of heterocyclyl or heteroaryl residues comprises: thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl and isoxazolyl.

"Heterocyclyloxy" or "heteroaryloxy" represent the oxygen-linked analogs of the above heterocyclyl or heteroaryl residues.

A specific sub-group of the above heterocyclyl residues are "heterocycloalkyl" residues. This group comprises saturated cycloaliphatic groups having 4 to 7, preferably 5 or 6 ring atoms, in which 1, 2, 3 or 4 of the ring carbon atoms have been replaced by heteroatoms, preferably selected from N, O and S and which may be optionally substituted. In the case of a substitution, these heterocycloaliphatic groups preferably have 1, 2 or 3, particularly preferably 1 or 2, particularly 1 substituent(s). These are preferably selected from Group 1 substituents above. By way of example of such heterocycloaliphatic residues, mention may be made of pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

"Heterocycloalkoxy" represents especially the above alkoxy groups bearing at least one of the heterocyclyl residues mentioned above as substituents.

"Arylene", "heteroarylene" and "heteroalkylene" bridging groups according to the invention correspond to the double-linked analogs of the above aryl, heteroaryl and heteroalkyl groups.

"Condensed ring systems" may be aromatic, hydroaromatic and cyclic compounds linked (condensed on) by fusion. Condensed ring systems consist of two, three or more than three rings. Depending on the type of linkage, condensed ring systems are differentiated between an ortho-fusion, i.e. each ring has an edge or two atoms in common with each neighbouring ring, and a peri-fusion, in which one carbon atom belongs to more than two rings. Condensed ring systems are preferably ortho-condensed ring systems.

b5) Miscellaneous

"Acyl" in the context of the present invention represents alkanoyl or aroyl groups having in general 2 to 11, preferably 2 to 8 carbon atoms, for example, the acetyl, propanoyl, butanoyl, pentanoyl, hexanoyl, heptanoyl, 2-ethylhexanoyl, 2-propylheptanoyl, benzoyl or naphthoyl group.

"Metallocene" in accordance with the invention represents a group of organometallic compounds, in which a central metal atom Me, particularly Fe, is arranged as in a sandwich between two cyclopentadienyl ligands ($C_5H_5$, abbreviation: Cp). "Metallocenyl" represents a side group derived from such a sandwich compound, which is bound to a molecule via at least one Cp ring carbon atom.

The groups $NE^1E^2$, $NE^4E^5$, $NE^9E^{10}$, are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

"Halogen" represents fluorine, chlorine, bromine and iodine, preferably fluorine, chlorine and bromine.

"$M^+$" is one cation equivalent, i.e. a monovalent cation or the proportion of a polyvalent cation corresponding to a single positive charge. The cation $M^+$ serves only as counterion for neutralizing negatively charged substituent groups, such as the COO— or the sulfonate group and can in principle be freely chosen. Preference is given, therefore, to using alkali metal ions, particularly $Na^+$, $K^+$ or $Li^+$ ions or onium ions such as ammonium, mono-, di-, tri- and tetraalkylammonium, phosphonium, tetraalkylphosphonium or tetraarylphosphonium ions.

The same applies to the anion equivalent "$X^-$", which serves only as counterion for positively charged substituent groups, such as ammonium groups, and to the proportion of a monovalent anion corresponding to a single negative charge, and may be freely chosen from monovalent anions. Suitable anions are, for example, halide ions $X^-$ such as chloride and bromide. Preferred anions are sulfate and sulfonate, e.g. $SO_4^{2-}$, tosylate, trifluoromethanesulfonate and methylsulfonate.

The definitions detailed in this section also apply to specific aspects of the invention unless otherwise stated.

c) Particular Embodiments of the Invention:

The present invention relates particularly to:

1. A method for the reductive amination of a carbonyl compound, comprising one or more, for example 1, 2, 3, 4 or 5, particularly 1, 2 or 3, preferably 1 carbonyl group(s) amenable to reductive amination, characterized in that the reaction is carried out in the presence of a homogeneously dissolved catalyst K and an acid as co-catalyst, in which K comprises at least one metal atom from Group 8, 9 or 10 of the periodic table (IUPAC), particularly from Group 8 or 9, preferably from Group 8 (Fe, Ru, Os), a bidentate phosphane ligand, a carbonyl ligand (CO), a hydride ligand (H) and optionally a neutral ligand ($L_N$).

2. The method according to embodiment 1, wherein the catalyst K is a ruthenium catalyst.

3. The method according to either of the preceding embodiments, wherein the bidentate phosphane ligand has the following general formula III:

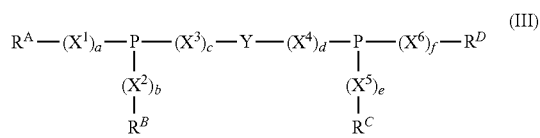

where
a, b, c, d, e and f are mutually independently 0 or 1,
$X^1$, $X^2$, $X^3$, $X^4$, $X^5$ and $X^6$ are mutually independently alkylene, arylene, O, S, —(C=O)-$NE^7$-metallocenyl, metallocenyl-$NE^7$-(C=O)—, —(C=O)-$NE^7$-, -$NE^7$-(C=O)— or $NE^8$, where $E^8$ is H or an alkyl, cycloalkyl, heterocyclyl, aryl or a hetaryl residue, and $E^7$ is H or an alkyl residue; wherein said residues and the metallocenyl, alkylene or arylene groups are each mutually independently optionally mono- or polysubstituted, in particular bearing 1, 2, 3, 4 or 5, preferably 1 or 2, substituents or are unsubstituted, and wherein the substituents are mutually independently selected from alkyl, cycloalkyl, heterocyclyl, aryl, hetaryl, alkoxy, cycloalkoxy, heterocycloalkoxy, aryloxy, hetaryloxy, hydroxyl, mercapto, polyalkylene oxide, polyalkylenimine, COOH, carboxylate, $SO_3H$, sulfonate, halogen, nitro, formyl, acyl, cyano, $NE^1E^2$, and $NE^1E^2E^{3+}X^-$, where $E^1$, $E^2$ and $E^3$ are each identical or different residues selected from hydrogen, alkyl, cycloalkyl, or aryl and $X^-$ is an anion equivalent,
Y is a divalent carbon atom-containing bridging group, and
$R^A$, $R^B$, $R^C$ and $R^D$ are residues mutually independently selected from alkyl, cycloalkyl, heterocycloalkyl, aryl or hetaryl, wherein said residues are mutually independently optionally mono- or polysubstituted, in particular bearing 1, 2, 3, 4 or 5, preferably 1 or 2, substituents or are unsubstituted, wherein the substituents are mutually independently selected from alkyl, cycloalkyl, heterocyclyl, aryl, hetaryl, alkoxy, cycloalkoxy, heterocycloalkoxy, aryloxy, hetaryloxy, hydroxyl, mercapto, polyalkylene oxide, polyalkylenimine, COOH, carboxylate, $SO_3H$, sulfonate, halogen, nitro, formyl, acyl, cyano, $NE^1E^2$, and $NE^1E^2E^{3+}X^-$, where $E^1$, $E^2$ and $E^3$ are each identical or different residues selected from hydrogen, alkyl, cycloalkyl, or aryl and $X^-$ is an anion equivalent;
or
$R^A$ and $R^B$ and/or $R^C$ and $R^D$ together with the phosphorus atom and, if present, the groups $X^1$, $X^2$, $X^5$ and $X^6$ to which they are bound, are a 4- to 8-membered heterocycle or heterobicycle, which optionally additionally bear in particular 1, 2 or 3 substituents, preferably 1 or 2 substituents, or are unsubstituted, and is fused to cycloalkyl, heterocyclyl, aryl or hetaryl, wherein the heterocycle or heterobicycle and, if present, the fused groups, are mutually independently optionally substituted, in particular bearing 1, 2, 3, 4 or 5 substituents, preferably 1 or 2 substituents or are unsubstituted, wherein the substituents are selected from alkyl, cycloalkyl, heterocyclyl, aryl, hetaryl, hydroxyl, mercapto, polyalkylene oxide, polyalkylenimine, alkoxy, halogen, COOH, carboxylate, $SO_3H$, sulfonate, $NE^4E^5$, $NE^4E^5E^{6+}X^-$, nitro, alkoxycarbonyl, formyl, acyl and cyano, where $E^4$, $E^5$ and $E^6$ are each identical or different residues selected from hydrogen, alkyl, cycloalkyl and aryl and $X^-$ is an anion equivalent;
or
one of the residues $R^A$ and $R^B$ and/or one of the residues $R^C$ and $R^D$ together with the phosphorus atom and, if present, the groups $X^1$, $X^2$, $X^5$ and $X^6$ to which they are bound, and together with a bridging group atom of the bridging group Y, are a 5- to 8-membered heterocycle, which optionally additionally bear in particular 1, 2, 3, 4 or 5 substituents, preferably 1 or 2 substituents, or are unsubstituted, and is fused to cycloalkyl, heterocycloalkyl, aryl or hetaryl, wherein the heterocycle and, if present, the fused groups, are mutually independently optionally additionally substituted, in particular bearing 1, 2, 3, 4 or 5 substituents, preferably 1 or 2 substituents, or are unsubstituted, wherein the substituents are selected from alkyl, cycloalkyl, heterocyclyl, aryl, hetaryl, hydroxyl, mercapto, polyalkylene oxide, polyalkylenimine, alkoxy, halogen, COOH, carboxylate, $SO_3H$, sulfonate, $NE^4E^5$, $NE^4E^5E^{6+}X^-$, nitro, alkoxycarbonyl, formyl, acyl and cyano, where $E^4$, $E^5$ and $E^6$ are each identical or different residues selected from hydrogen, alkyl, cycloalkyl and aryl and $X^-$ is an anion equivalent.

In formula III above, the following definitions particularly apply:
Alkylene particularly represents $C_1$-$C_{10}$-alkylene;
Arylene particularly represents $C_5$-$C_{20}$-arylene;
Alkyl particularly represents $C_1$-$C_{30}$-alkyl;
Cycloalkyl particularly represents $C_5$-$C_{30}$-cycloalkyl;
Metallocenyl is particularly ferrocenyl;
Heterocyclyl particularly represents mono-, bi- or tricyclic groups having 1 to 30 ring carbon atoms and 1 to 4 ring heteroatoms selected from O, N and S;
Heterocycloalkyl particularly represents mono-, bi- or tricyclic groups having 1 to 30 ring carbon atoms and 1 to 4 ring heteroatoms selected from O, N and S, bonded to a $C_1$-$C_{30}$-alkyl residue;
Aryl particularly represents mono-, bi-, tri- or tetracyclic, optionally substituted aromatic residues having 5 to 20 ring carbon atoms;
Hetaryl particularly represents a group having 1 to 30 ring carbon atoms and at least one five- to seven-membered aromatic ring;
Alkoxy particularly represents the oxygen-linked analogs of the above $C_1$-$C_{30}$-alkyl residues;
Cycloalkoxy particularly represents the oxygen-terminated analogs of carbocyclic, mono- or polycyclic, e.g. mono-, bi- or tricyclic, residues having 3 to 30 carbon atoms; Heterocycloalkoxy particularly represents the above $C_1$-$C_{30}$-alkoxy groups which bear at least one of the abovementioned heterocyclyl residues as substituents, having mono-, bi- or tricyclic groups with 1 to 30 ring carbon atoms and 1 to 4 ring heteroatoms selected from O, N and S;
Aryloxy particularly represents the oxygen-linked analogs of the above aryl residues having 5 to 20 ring carbon atoms;
Hetaryloxy particularly represents the oxygen-linked analogs of the above heteroaryl residues having 1 to 30 ring carbon atoms and at least one five- to seven-membered aromatic ring;
Polyalkylene oxide represents in particular a residue derived from the same or different $C_{2-4}$-oxyalkylene monomer units having a degree of polymerization of 2 to 100;
Polyalkylenimine particularly represents the structurally analogous imine group-containing residues of the above polyalkyene oxide residues;
Acyl particularly represents alkanoyl or aroyl groups having 2 to 11 carbon atoms; and
Alkoxycarbonyl particularly represents the carbonyl-linked analogs of the above $C_1$-$C_{30}$-alkoxy residues.

4. The method according to embodiment 3, wherein the bidentate phosphane ligand is selected from compounds of the general formula III,
where
$X^1$, $X^2$, $X^3$, $X^4$, $X^5$ and $X^6$ are mutually independently optionally substituted $C_1$-$C_6$-alkylene, O, —(C=O)-$NE^7$-ferrocenyl, ferrocenyl-$NE^7$-(C=O)—, —(C=O)-$NE^7$- or -$NE^7$-(C=O)—, where $E^7$ is as defined above;

Y, a, b, c, d, e and f are as defined above;

$R^A$, $R^B$, $R^C$ and $R^D$ are residues mutually independently selected from $C_1$-$C_{30}$-alkyl, $C_4$-$C_{10}$-cycloalkyl, $C_3$-$C_{10}$-heterocyclyl, $C_5$-$C_{14}$-aryl or $C_5$-$C_{30}$-hetaryl, wherein said residues are mutually independently optionally mono- or polysubstituted, in particular bearing 1, 2, 3, 4 or 5, e.g. 1 or 2 substituents, wherein the substituents are mutually independently selected from $C_1$-$C_{10}$-alkyl, $C_4$-$C_{10}$-cycloalkyl, $C_3$-$C_{10}$-heterocloalkyl, $C_5$-$C_{14}$-aryl, $C_5$-$C_{30}$-hetaryl, $C_1$-$C_{10}$-alkoxy, $C_3$-$C_{10}$-cycloalkoxy, $C_3$-$C_{10}$-heterocycloalkoxy, $C_5$-$C_{14}$-aryloxy, $C_5$-$C_{30}$-hetaryloxy, hydroxyl, mercapto, poly-$C_2$-$C_6$-alkylene oxide, poly-$C_2$-$C_6$-alkylenimine, COOH, carboxylate, $SO_3H$, sulfonate, halogen, nitro, formyl, $C_1$-$C_{10}$-acyl, cyano, $NE^1E^2$, and $NE^1E^2E^{3+}X^-$, where $E^1$, $E^2$ and $E^3$ are each identical or different residues selected from hydrogen, $C_1$-$C_{10}$-alkyl, $C_3$-$C_{10}$-cycloalkyl, or $C_5$-$C_{10}$-aryl and $X^-$ is an anion equivalent;

or $R^A$ and $R^B$ and/or $R^C$ and $R^D$ together with the phosphorus atom and, if present, the groups $X^1$, $X^2$, $X^5$ and $X^6$ to which they are bound, are a 4- to 8-membered heterocycle or heterobicycle, which is optionally additionally, in particular singly, doubly or triply fused to $C_4$-$C_{10}$-cycloalkyl, $C_3$-$C_{10}$-heterocycloalkyl, $C_5$-$C_{14}$-aryl or $C_5$-$C_{30}$-hetaryl, wherein the heterocycle or heterobicycle and, if present, the fused groups, are mutually independently optionally substituted, in particular each possibly bearing one, two, three or four substituents, wherein the substituents are selected from $C_1$-$C_{10}$-alkyl, $C_3$-$C_{10}$-cycloalkyl, $C_3$-$C_{10}$-heterocycloalkyl, $C_5$-$C_{14}$-aryl, $C_5$-$C_{30}$-hetaryl, hydroxyl, mercapto, poly-$C_2$-$C_6$-alkylene oxide, poly-$C_2$-$C_6$-alkylenimine, $C_1$-$C_{10}$-alkoxy, halogen, COOH, carboxylate, $SO_3H$, sulfonate, $NE^4E^5$, $NE^4E^5E^{6+}X^-$, nitro, $C_1$-$C_{10}$-alkoxycarbonyl, formyl, $C_1$-$C_{10}$-acyl and cyano, where $E^4$, $E^5$ and $E^6$ are each identical or different residues selected from hydrogen, $C_1$-$C_{10}$-alkyl, $C_3$-$C_{10}$-cycloalkyl and $C_5$-$C_{14}$-aryl and $X^-$ is an anion equivalent;

or one of the residues $R^A$ and $R^B$ and/or one of the residues $R^C$ and $R^D$ together with the phosphorus atom and, if present, the groups $X^1$, $X^2$, $X^5$ and $X^6$ to which they are bound, and together with a bridging group atom of the bridging group Y, are a 5- to 8-membered heterocycle, which is optionally additionally, in particular singly, doubly or triply fused to $C_3$-$C_{10}$-cycloalkyl, $C_3$-$C_{10}$-heterocycloalkyl, $C_5$-$C_{14}$-aryl or $C_5$-$C_{30}$-hetaryl, wherein the heterocycle and, if present, the fused groups, are in addition mutually independently optionally, particularly mono-, bi-, tri- or tetrasubstituted, wherein the substituents are selected from $C_1$-$C_{10}$-alkyl, $C_3$-$C_{10}$-cycloalkyl, $C_3$-$C_{10}$-heterocycloalkyl, $C_5$-$C_{14}$-aryl, $C_5$-$C_{30}$-hetaryl, hydroxyl, mercapto, poly-$C_2$-$C_6$-alkylene oxide, poly-$C_2$-$C_6$-alkylenimine, $C_1$-$C_{10}$-alkoxy, halogen, COOH, carboxylate, $SO_3H$, sulfonate, $NE^4E^5$, $NE^4E^5E^{6+}X^-$, nitro, $C_1$-$C_{10}$-alkoxycarbonyl, formyl, $C_1$-$C_{10}$-acyl and cyano, where $E^4$, $E^5$ and $E^6$ are each identical or different residues selected from hydrogen, $C_1$-$C_{10}$-alkyl, $C_3$-$C_{10}$-cycloalkyl and $C_5$-$C_{14}$-aryl and $X^-$ is an anion equivalent.

5. The method according to any of the preceding embodiments, wherein the group Y in the bidentate phosphane ligand of the general formula III is a bridging group selected from straight-chain or branched alkylene, particularly $C_1$-$C_6$-alkylene, preferably —$CH_2$—$CH(CH_3)$—, —CH($CH_3$)—$CH_2$—, —$CH(CH_3)$—$CH(CH_3)$—;

straight-chain or branched alkenylene, particularly $C_2$-$C_6$-alkenylene, cycloalkylene, particularly $C_3$-$C_{30}$-cycloalkylene, preferably $C_3$-$C_{12}$-cycloalkylene, optionally comprising at least one ring heteroatom, particularly 1 or 2 identical or different, preferably identical, ring heteroatoms, selected from N, O, S, cycloalkenylene, particularly $C_3$-$C_{30}$-cycloalkenylene, preferably $C_3$-$C_{12}$-cycloalkenylene, optionally comprising at least one ring heteroatom, particularly 1 or 2 identical or different, preferably identical, ring heteroatoms, selected from N, O, S, bi-, tri- and tetracyclic bridging groups;

arylene, particularly mono-, bi- or tricyclic $C_5$-$C_{14}$-arylene, preferably o-phenylene, heteroarylene, particularly $C_5$-$C_6$-heteroarylene, comprising at least one ring heteroatom, particularly 1 or 2 identical or different, preferably identical, ring heteroatoms, selected from N, O and S, heteroalkylene, particularly $C_2$-$C_6$-heteroalkylene, comprising at least one chain heteroatom, particularly 1 or 2 identical or different, preferably identical, ring heteroatoms, selected from N, O and S, heteroalkenylene, particularly $C_2$-$C_6$-heteroalkenylene, comprising at least one chain heteroatom, particularly 1 or 2 identical or different, preferably identical, heteroatoms, selected from N, O and S, polycyclic, particularly bi-, tri-, tetra-, penta- or hexacyclic bridging groups comprising at least two mutually bound aromatic, heteroaromatic, carbocyclic or heterocyclic, 4- to 8-membered rings; and metallocene bridging groups comprising at least one metallocene group of the general formula

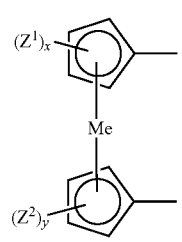

where Me is a metal atom, particularly Fe, wherein the phosphorus atoms of the phosphane ligands are bonded directly or via one of the groups $X^3$ or $X^4$, preferably directly, to the same or two different Cp rings of the metallocene, preferably to two different Cp rings of the metallocene, x and y are mutually independently 0, 1, 2, 3 or 4 and $Z^1$ and $Z^2$ are mutually independently H, optionally mono- or polysubstituted alkyl, particularly $C_1$-$C_6$-alkyl or optionally mono- or polysubstituted aryl, in particular $C_5$-$C_{12}$-aryl; and wherein the substituents are mutually independently selected from $C_1$-$C_{10}$-alkyl, $C_4$-$C_{10}$-cycloalkyl, $C_3$-$C_{10}$-heterocycloalkyl, $C_5$-$C_{14}$-aryl, $C_5$-$C_{30}$-hetaryl, $C_1$-$C_{10}$-alkoxy, $C_3$-$C_{10}$-cycloalkoxy, $C_3$-$C_{10}$-heterocycloalkoxy, $C_5$-$C_{14}$-aryloxy, $C_5$-$C_{30}$-hetaryloxy, hydroxyl, mercapto, poly-$C_2$-$C_6$-alkylene oxide, poly-$C_2$-$C_6$-alkylenimine, COOH, carboxylate, $SO_3H$, sulfonate, halogen, nitro, formyl, $C_1$-$C_{10}$-acyl, cyano, $NE^1E^2$, and NE¹E²E³⁺X⁻, where $E^1$, $E^2$ and $E^3$ are in each case identical or different residues selected from hydrogen, $C_1$-$C_{10}$-alkyl, $C_3$-$C_{10}$-cycloalkyl, or $C_5$-$C_{10}$-aryl and $X^-$ is an anion equivalent.

6. The method according to any of the preceding embodiments, wherein the group Y in the bidentate phosphane ligand of the general formula III is a polycyclic bridging group selected from groups of the formulae III.a to III.k

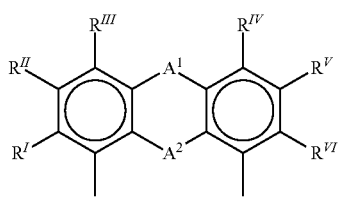
(III.a)

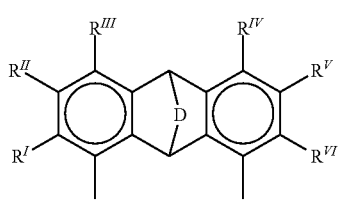
(III.b)

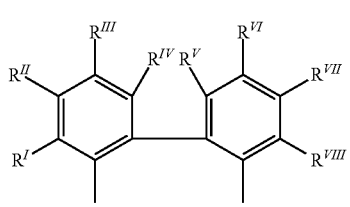
(III.c)

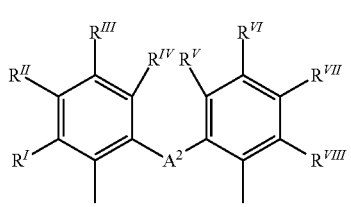
(III.d)

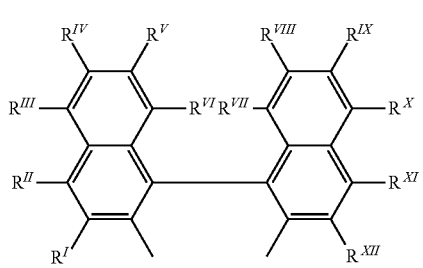
(III.e)

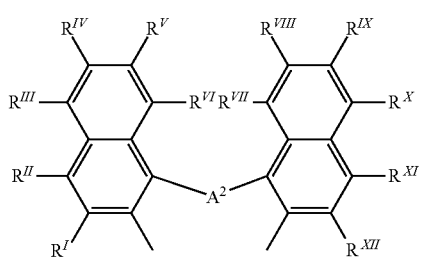
(III.f)

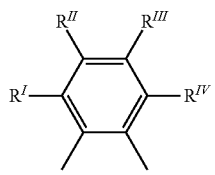
(III.g)

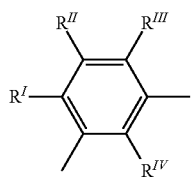
(III.h)

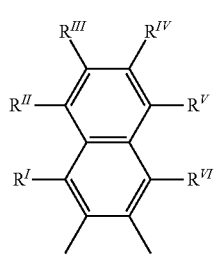
(III.i)

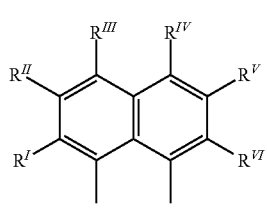
(III.k)

where $R^I$, $R^{II}$, $R^{III}$, $R^{IV}$, $R^V$, $R^{VI}$, $R^{VII}$, $R^{VIII}$, $R^{IX}$, $R^X$, $R^{XI}$ and $R^{XII}$ are mutually independently hydrogen, alkyl, cycloalkyl, heterocycloalkyl, aryl, hetaryl, hydroxyl, mercapto, polyalkylene oxide, polyalkylenimine, alkoxy, halogen, $SO_3H$, sulfonate, $NE^9E^{10}$, alkylene-$NE^9E^{10}$, trifluoromethyl, nitro, alkoxycarbonyl, carboxyl, formyl, acyl or cyano, where $E^9$ and $E^{10}$ are each identical or different residues selected from hydrogen, alkyl, cycloalkyl and aryl, or in each case two adjacent residues $R^I$, $R^{II}$, $R^{III}$, $R^{IV}$, $R^V$, $R^{VI}$, $R^{VII}$, $R^{VIII}$, $R^{IX}$, $R^X$, $R^{XI}$ and $R^{XII}$, together with the carbon atoms to which they are bound, form a 4- to 7-membered carbocyclic or heterocyclic, aromatic or non-aromatic ring, which in turn may optionally be fused to a mono- or polycyclic carbocyclic or heterocyclic, aromatic or non-aromatic ring, wherein said ring system is optionally, particularly mono-, bi- or trisubstituted, wherein the substituents are selected from alkyl, cycloalkyl, heterocyclyl, aryl, hetaryl, hydroxyl, mercapto, polyalkylene oxide, polyalkylenimine, alkoxy, halogen, COOH, carboxylate, $SO_3H$, sulfonate, $NE^4E^5$, $NE^4E^5E^{6+}X^-$, nitro, alkoxycarbonyl, formyl, acyl and cyano, where $E^4$, $E^5$ and $E^6$ are each identical or different residues selected from hydrogen, alkyl, cycloalkyl and aryl and $X^-$ is an anion equivalent;

where the two adjacent residues from the group $R^I$, $R^{II}$, $R^{III}$, $R^{IV}$, $R^V$, $R^{VI}$, $R^{VII}$, $R^{VIII}$, $R^{IX}$, $R^X$, $R^{XI}$ and $R^{XII}$ may be bound to carbon atoms of the same aromatic ring or to carbon atoms of two different, preferably adjacent aromatic rings, such as for example $R^{IV}$ and $R^V$ in the formulae (III.c) and (III.d) or $R^{VI}$ and $R^{VII}$ or $R^V$ and $R^{VIII}$ in the formulae (III.e) and (III.f);

$A^1$ is a bond, NH, $NR^{11}$, O, S, $CR^{11}$ or $CR^{11}R^{12}$, where $R^{11}$ and $R^{12}$ are mutually independently selected from alkyl, aryl and H;

$A^2$ is an NH— group, N, O or S,

D is a divalent bridging group of the general formula

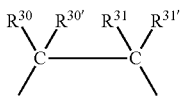

in which $R^{30}$, $R^{30'}$, $R^{31}$ and $R^{31'}$ are mutually independently hydrogen, alkyl, cycloalkyl, aryl, halogen, trifluoromethyl, carboxyl, carboxylate or cyano, where $R^{30'}$ together with $R^{31'}$ can also be the second bond of a double bond between the two carbon atoms to which $R^{30'}$ and $R^{31'}$ are bound, and/or $R^{30}$ and $R^{31}$ together with the carbon atoms to which they are bound can also be a 4- to 8-membered carbocycle or heterocycle, which in addition is optionally singly, doubly or triply fused with cycloalkyl, heterocycloalkyl, aryl or hetaryl, wherein the carbocycle or heterocycle and, if present, the fused groups may each mutually independently bear one, two, three or four substituents selected from alkyl, cycloalkyl, heterocycloalkyl, aryl, hetaryl, $COOR^e$, $COO^-M^+$, $SO_3R^e$, $SO_3^-M^+$, $NE^{11}E^{12}$, alkylene-$NE^{11}E^{12}$, $NE^{11}E^{12}E^{13+}X^-$, alkylene-$NE^{11}E^{12}E^{13+}X^-$, $OR^e$, $SR^e$, $(CHR^fCH_2O)_yR^e$, $(CH_2N(E^{11}))_yR^e$, $(CH_2CH_2N(E^{11}))_yR^e$, halogen, trifluoromethyl, nitro, formyl, acyl or cyano, where $R^e$, $E^{11}$, $E^{12}$ and $E^{13}$ are each identical or different residues selected from hydrogen, alkyl, cycloalkyl or aryl, $R^f$ is hydrogen, methyl or ethyl, $M^+$ is a cation equivalent, $X^-$ is an anion equivalent, and y is an integer from 1 to 120.

In the above formulae III.a to III.k, the following definitions particularly apply:

Alkylene particularly represents $C_1$-$C_{10}$-alkylene;
Arylene particularly represents $C_5$-$C_{20}$-arylene;
Alkyl particularly represents $C_1$-$C_{30}$-alkyl;
Cycloalkyl particularly represents $C_5$-$C_{30}$-cycloalkyl;
Metallocenyl is particularly ferrocenyl;
Heterocyclyl particularly represents mono-, bi- or tricyclic groups having 1 to 30 ring carbon atoms and 1 to 4 ring heteroatoms selected from O, N and S;
Heterocycloalkyl particularly represents mono-, bi- or tricyclic groups having 1 to 30 ring carbon atoms and 1 to 4 ring heteroatoms selected from O, N and S, bonded to a $C_1$-$C_{30}$-alkyl residue;
Aryl particularly represents mono-, bi-, tri- or tetracyclic, optionally substituted aromatic residues having 5 to 20 ring carbon atoms;
Hetaryl particularly represents a group having 1 to 30 ring carbon atoms and at least one five- to seven-membered aromatic ring;
Alkoxy particularly represents the oxygen-linked analogs of the above $C_1$-$C_{30}$-alkyl residues;
Cycloalkoxy particularly represents the oxygen-terminated analogs of carbocyclic, mono- or polycyclic, e.g. mono-, bi- or tricyclic, residues having 3 to 30 carbon atoms;

Heterocycloalkoxy particularly represents the above $C_1$-$C_{30}$-alkoxy groups which bear at least one of the above-mentioned heterocyclyl residues as substituents, having mono-, bi- or tricyclic groups with 1 to 30 ring carbon atoms and 1 to 4 ring heteroatoms selected from O, N and S;

Aryloxy particularly represents the oxygen-linked analogs of the above aryl residues having 5 to 20 ring carbon atoms;

Hetaryloxy particularly represents the oxygen-linked analogs of the above heteroaryl residues having 1 to 30 ring carbon atoms and at least one five- to seven-membered aromatic ring;

Polyalkylene oxide represents in particular a residue derived from the same or different $C_{2-4}$-oxyalkylene monomer units having a degree of polymerization of 2 to 100;

Polyalkylenimine particularly represents the structurally analogous imine group-containing residues of the above polyalkyene oxide residues;

Acyl particularly represents alkanoyl or aroyl groups having 2 to 11 carbon atoms; and Alkoxycarbonyl particularly represents the carbonyl-linked analogs of the above $C_1$-$C_{30}$-alkyl residues.

If in formula III.a $A^1$ is $CR^{11}$ (i.e. —$C(R^{11})$=) and $A^2$ is N (i.e. —N=), a bridging group having an acridine structure is obtained.

7. The method according to any of the preceding embodiments, wherein the group Y in the bidentate phosphane ligand of the general formula III is a bridging group selected from polycyclic groups III.m to III.o

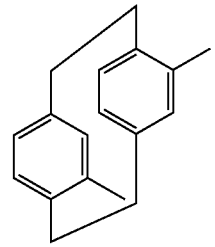

(III.m)

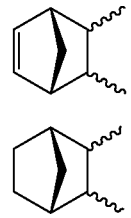

(III.n)

(III.o)

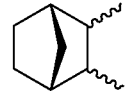

8. The method according to any of the preceding embodiments, wherein the group Y in the bidentate phosphane ligand of the general formula III is a bridging group selected from the heterocyclic groups V.a to V.g

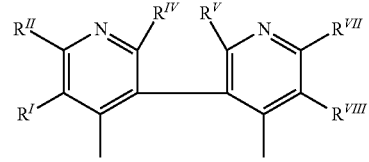

(V.a)

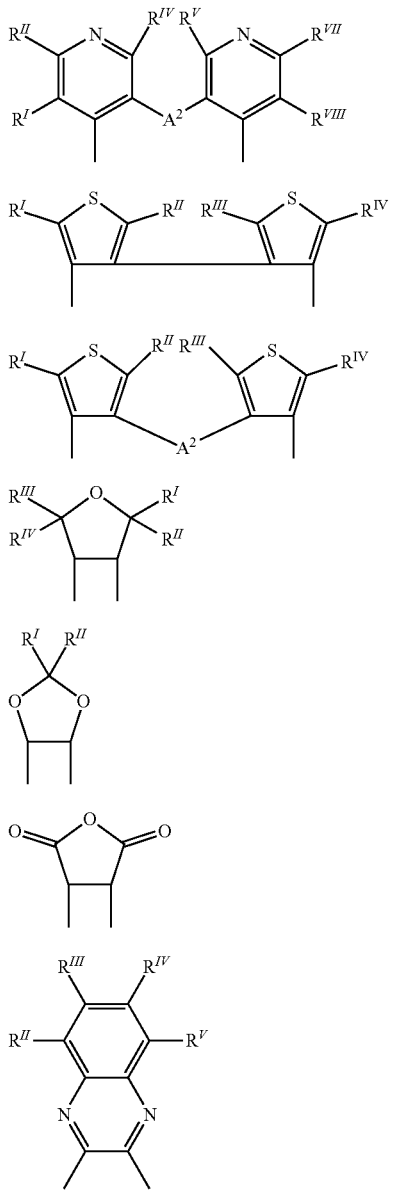

(V.b)
(V.c)
(V.d)
(V.e)
(V.f)
(V.g)
(V.h)

where
the residues $R^I$ to $R^{VIII}$ are mutually independently selected from hydrogen, alkyl, cycloalkyl, heterocycloalkyl, aryl, hetaryl, hydroxyl, mercapto, polyalkylene oxide, polyalkylenimine, alkoxy, halogen, $SO_3H$, sulfonate, $NE^9E^{10}$, alkylene-$NE^9E^{10}$, trifluoromethyl, nitro, alkoxycarbonyl, carboxyl, formyl, acyl or cyano, where $E^9$ and $E^{10}$ are each identical or different residues selected from hydrogen, alkyl, cycloalkyl and aryl; and
$A^2$ is NH, N, O or S.

In the above formulae V.a to V.h, the following definitions particularly apply:
Alkylene particularly represents $C_1$-$C_{10}$-alkylene;
Alkyl particularly represents $C_1$-$C_{30}$-alkyl;
Cycloalkyl particularly represents $C_5$-$C_{30}$-cycloalkyl;
Heterocycloalkyl particularly represents mono-, bi- or tricyclic groups having 1 to 30 ring carbon atoms and 1 to 4 ring heteroatoms selected from O, N and S, bonded to a $C_1$-$C_{30}$-alkyl residue;

Aryl particularly represents mono-, bi-, tri- or tetracyclic, optionally substituted aromatic residues having 5 to 20 ring carbon atoms;
Hetaryl particularly represents a group having 1 to 30 ring carbon atoms and at least one five- to seven-membered aromatic ring;
Alkoxy particularly represents the oxygen-linked analogs of the above $C_1$-$C_{30}$-alkyl residues;
Polyalkylene oxide represents in particular a residue derived from the same or different $C_{2\text{-}4}$-oxyalkylene monomer units having a degree of polymerization of 2 to 100;
Polyalkylenimine particularly represents the structurally analogous imine group containing residues of the above polyalkylene oxide residues; and
Acyl particularly represents alkanoyl or aroyl groups having 2 to 11 carbon atoms; and
Alkoxycarbonyl particularly represents the carbonyl-linked analogs of the above $C_1$-$C_{30}$-alkyl residues.

9. The method according to any of the preceding embodiments, wherein the two phosphane end groups in the bidentate phosphane ligand of the general formula III are mutually independently selected from groups of the formulae VI.a to VI.k

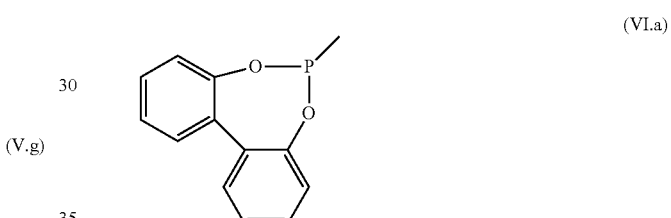

(VI.a)

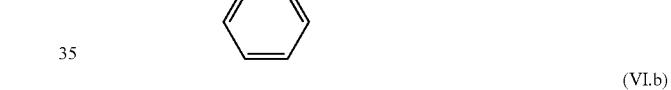

(VI.b)

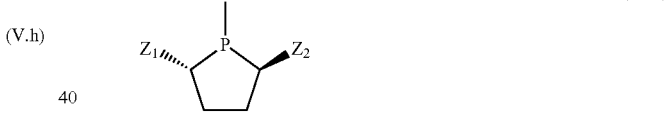

(VI.c)

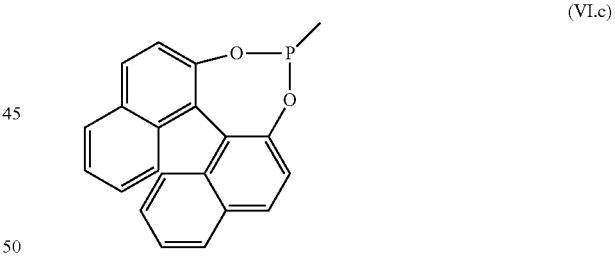

(VI.d)

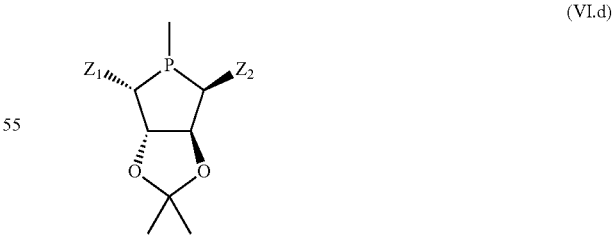

(VI.e)

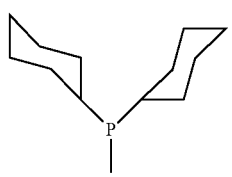

-continued

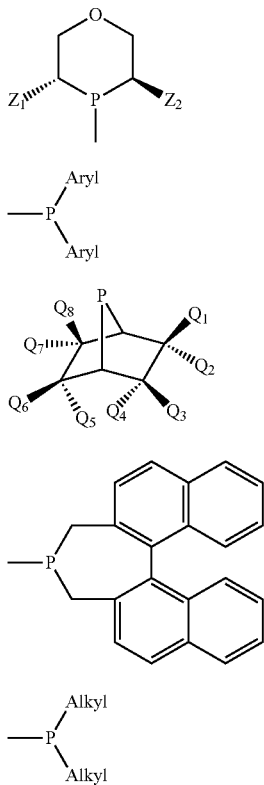

(VI.f)

(VI.g)

(VI.h)

(VI.k)

(VI.i)

where
aryl is phenyl, optionally mono- or polysubstituted, wherein the substituents are selected from alkyl or alkoxy
$Z_1$ and $Z_2$ are mutually independently selected from alkyl, alkoxy, alkoxyalkyl, aryl or hetaryl and
$Q_1$ to $Q_8$ are mutually independently H or alkyl.

In the above formulae VI.a to VI.k, the following definitions particularly apply:
Alkyl particularly represents $C_1$-$C_{30}$-alkyl;
Alkoxy particularly represents the oxygen-linked analogs of the above $C_1$-$C_{30}$-alkyl residues;
Aryl particularly represents mono-, bi-, tri- or tetracyclic, optionally substituted aromatic residues having 5 to 20 ring carbon atoms;
Hetaryl particularly represents a group having 1 to 30 ring carbon atoms and at least one five- to seven-membered aromatic ring;
Alkoxyalkyl particularly represents the above $C_1$-$C_{30}$-alkyl groups bearing at least one of the $C_1$-$C_{30}$-alkoxy residues mentioned above as substituents.

With respect to the above embodiments 3 to 9 the following preferred definitions apply to compounds of the formula III:
(1) a, b, e and f are 0 or
(2) a, b, c, d, e and f are 0
(3) $R^A$, $R^B$, $R^C$ and $R^D$ are in particular identical and are optionally mono- or bisubstituted aryl, particularly optionally mono- or bisubstituted phenyl; substituents are preferably $C_1$-$C_4$-alkyl residues
(4) Y is a straight-chain or branched alkylene having 2 to 5 carbon atoms, in particular the bridging group may have 1 or 2 asymmetric centres (asymmetric carbon atoms)

(5) Y is a group of the formula III.e where $R^I$ to $R^{XII}$ are H
(6) Y is a group of the formula III.d where $R^I$ to $R^{VIII}$ are H and $A^2$ is O,
(7) Y is a group of the formula III.g where $R^I$ to $R^{IV}$ are H Particularly preferred embodiments of ligands of the formula III comprise combinations of the above definitions (1) or (2) with (3) and one of the definitions (4) to (7).
With respect to the above embodiment 8 the following preferred definitions apply to compounds of the formula V:
(1) $A^2$ is O or S;
(2) $R^I$ to $R^{VIII}$ are H.

10. The method according to any of the preceding embodiments, wherein the acid co-catalyst is a Lewis acid.
11. The method according to any of the preceding embodiments, wherein the acid co-catalyst is selected from: $[NH_4]TFA$, $[NH_4]Cl$, $[NH_4]_2[SO_4]$, $[NH_4]Br$, $Al(OTf)_3$, $Sc(OTf)_3$, $AlCl_3$, $AlBr_3$, $BR_3$, $BCl_3$, $BBr_3$, $BF_3$ NaPF and $Al(NO_3)_3$, particularly $[NH_4]TFA$, $Al(OTf)_3$, $Sc(OTf)_3$ and $AlCl_3$.
12. The method according to any of the preceding embodiments, wherein the catalyst K is a ruthenium catalyst having the following general formula IV

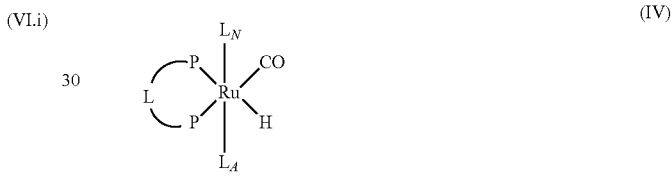

(IV)

where
P-L-P is the bidentate phosphane ligand of the formula (III) defined above;
$L_N$ is a neutral ligand selected from amines, phosphanes, phosphites, alcohols, N-heterocyclic carbenes, imines, carbonyl compounds, olefins, alkynes or nitriles, particularly phosphanes and amines, most preferably triarylphosphanes and $NH_3$,
and
$L_A$ is absent or is an anionic ligand selected from chloride, fluoride, bromide, iodide, hydride, cyanide, alkoxy, amido or hydroxyl, particularly chloride or hydride.
13. The method according to any of the preceding embodiments, wherein the amination is carried out enantioselectively by using a catalyst K bearing at least one chiral bidentate phosphane ligand according to formula III above, particularly ligands of the formulae (1) to (86), and especially of the formulae (1), (9), (13), (20), (22) with n=3, (24) and (74).
14. The method according to any of the preceding embodiments, wherein the carbonyl compound to be aminated is a compound of the following general formula II,

(II)

where $R^1$ and $R^2$ are the same or different and are mutually independently selected from
H, optionally mono- or polysubstituted alkyl, particularly $C_1$-$C_{30}$-alkyl, preferably $C_1$-$C_{10}$-alkyl residues, wherein the carbon chain is optionally interrupted by one or more, e.g. 2, 3, 4 or 5, particularly 1 or 2, preferably 1, carbonyl groups; most preferred are $C_1$-$C_{10}$-alkyl residues without further carbonyl groups;

optionally mono- or polysubstituted cycloalkyl, particularly $C_3$-$C_{30}$-cycloalkyl, preferably $C_3$-$C_{12}$-cycloalkyl, wherein the carbocyclic ring is optionally interrupted by one or more, e.g. 2, 3, 4 or 5, particularly 1 or 2, preferably 1, carbonyl groups; most preferred are $C_3$-$C_{12}$-cycloalkyl residues without further carbonyl groups;

optionally mono- or polysubstituted heterocyclyl, particularly $C_3$-$C_{30}$-heterocyclyl, preferably $C_5$-$C_{12}$-heterocyclyl, comprising at least one heteroatom selected from N, O and S, wherein the heterocyclic ring is optionally interrupted by one or more, e.g. 2, 3, 4 or 5, particularly 1 or 2, preferably 1, carbonyl groups; most preferred are $C_3$-$C_{12}$-heterocyclyl residues without further carbonyl groups;

optionally mono- or polysubstituted mono-, bi- or tricyclic aryl, particularly $C_5$-$C_{14}$-aryl; and optionally mono- or polysubstituted mono-, bi- or tricyclic hetaryl, particularly $C_5$-$C_{14}$-heteroaryl, comprising at least one heteroatom selected from N, O and S;

where the substituents optionally present are selected from halogen, in particular F, Cl, Br, —OH, —CN, —$NH_2$, $C_1$-$C_{30}$-alkyl, $C_3$-$C_{30}$-cycloalkyl, $C_3$-$C_{30}$-heterocyclyl comprising at least one heteroatom selected from N, O and S, $C_5$-$C_{14}$-aryl, $C_5$-$C_{14}$-heteroaryl comprising at least one heteroatom selected from N, O and S, —$OR_7$, —$NHR_7$ or —$N(R_7)_2$, —$C(O)R_7$, —$C(O)OR_7$, —$C(O)NHR_7$ or —$C(O)N(R)_2$, where $R_7$ is selected from $C_1$-$C_{30}$-alkyl and $C_5$-$C_{30}$-aryl;

the substituents are preferably selected from F, Cl, Br, —OH, —CN, —$NH_2$, $C_1$-$C_{10}$-alkyl, $C_3$-$C_{12}$-cycloalkyl, $C_5$-$C_{12}$-heterocyclyl comprising at least one heteroatom selected from N, O and S, $C_5$-$C_{14}$-aryl, $C_5$-$C_{14}$-heteroaryl comprising at least one heteroatom selected from N, O and S, —$OR_7$, —$NHR_7$ or —$N(R_7)_2$, —$C(O)R_7$, —$C(O)OR_7$, —$C(O)NHR_7$ or —$C(O)N(R_7)_2$, where $R_7$ is selected from $C_1$-$C_{10}$-alkyl and $C_5$-$C_{14}$-aryl;

the substituents are particularly preferably selected from F, Cl, Br, —OH, —CN, —$NH_2$, $C_1$-$C_4$-alkyl, monocyclic cycloalkyl, monocyclic heterocyclyl, comprising at least one heteroatom selected from N, O and S, monocyclic aryl, monocyclic heteroaryl, comprising at least one heteroatom selected from N, O and S, —$OR_7$, —$NHR_7$ or —$N(R_7)_2$, —$C(O)R_7$, —$C(O)OR_7$, —$C(O)NHR_7$ or —$C(O)N(R_7)_2$, where $R_7$ is selected from $C_1$-$C_4$-alkyl and monocyclic aryl.

15. The method according to any of the preceding embodiments, wherein the catalyst K is formed from a catalyst precursor selected from the following compounds: [Ru(PPh$_3$)$_3$(H)(Cl)(CO)], [Ru(PPh$_3$)$_3$(H)$_2$(CO)], [Ru(PPh$_3$)$_3$(Cl)$_2$], [Ru(PPh$_3$)$_3$(Cl)$_2$(CO)], [Ru(p-cymene)(Cl)$_2$], [Ru(benzene)Cl$_2$]$_n$, [Ru(CO)$_2$Cp]$_n$, [Ru(CO)$_3$(Cl)$_2$], [Ru(COD)(allyl)], [Ru(COD)(2-methylallyl)$_2$], [RuCl$_2$*H$_2$O], [Ru(acetylacetonate)$_3$], [Ru(DMSO)$_4$(Cl)$_2$], Ru$_3$CO$_{12}$, [Ru(cyclopentadienyl)(PPh$_3$)$_2$(Cl)], [Ru(cyclopentadienyl)(CO)$_2$(Cl)], [Ru(cyclopentadienyl)(CO)$_2$H], [Ru(cyclopentadienyl)(CO)$_2$]$_2$, [Ru(pentamethylcyclopentadedienyl)(CO)$_2$(Cl)], [Ru(pentamethylcycloopentadienyl)(CO)$_2$H], [Ru(pentamethylcyclopentadienyl)(CO)$_2$]$_2$, [Ru(indenyl)(CO)$_2$(Cl)], [Ru(indenyl)(CO)$_2$(H)], [Ru(indenyl)(CO)$_2$]$_2$, ruthenocene, [Ru(binap)Cl$_2$], [Ru(bipyridine)$_2$Cl$_2$*2H$_2$O], [Ru(COD)Cl$_2$]$_2$, [Ru(pentamethylcyclopentadienyl)(COD)(Cl)], [Ru$_3$(CO)$_{12}$], [Ru(tetraphenylhydroxycyclopentadienyl)(CO)$_2$(H)], [Ru(PPh$_3$)$_4$(H)$_2$].

16. The method according to any of the preceding embodiments, wherein the catalyst K is used in an amount of 1 to 5000, 10 to 2000 or 100 to 1000 ppm parts by weight, based on the total weight of the liquid reaction medium used.

17. The method according to any of the preceding embodiments, wherein the reaction is carried out under the following reaction conditions:
a) temperature in the range of 20 to 250, particularly 50 to 150° C. and/or
b) total pressure in the range of 0.1 to 30, particularly 1 to 10 MPa and/or
c) reaction time of 0.1 to 100 h, particularly 5 to 30 and/or
d) ammonia: 1.5 to 250-fold, particularly 10 to 100-fold molar excess, based on the moles of reactant used and/or
e) hydrogen: 1.5 to 250-fold, particularly 10 to 100-fold molar excess, based on the moles of reactant used.

d) Reactants for the Reductive Amination Reaction According to the Invention

The reactants used in the method according to the invention are carbonyl compounds having the above general formula II.

In this case, the substituents $R^1$ and $R^2$ can be mutually independently defined as above. In the method according to the invention, the reactant may also comprise more, e.g. 2, 3, 4 or 5, particularly 2, but preferably only one carbonyl unit as functional group, which are aminated. If $R^1$ and $R^2$ are not the same and neither of the two substituents is hydrogen, it is then also possible in accordance with the invention to aminate this carbonyl compound enantioselectively.

$R^1$ and/or $R^2$ may also comprise one or more, e.g. 2, 3, 4 or 5, particularly 2, but preferably only one carboxyl group or derivatives thereof, such as amides, esters and nitriles, such that amino acid groups may be obtained by reductive amination.

Non-limiting examples of reactants according to formula II include: acetophenone, trifluoroacetophenone, trifluoromethylacetophenone, ketobutanol, indanone, 2-alkylindanone derivatives, 2-(benzyloxy)cyclopentanone, (1-naphthyl)acetone, (2-methoxyphenyl)acetone, (2-naphthyl)acetone, (3,4-dimethoxyphenyl)acetone, (3-bromophenyl)acetone, (3-chlorophenyl)acetone, (3-fluorophenyl)acetone, (4-methoxyphenyl)acetone, (4-methylphenyl)acetone, (3-pyridinyl)acetone, (2-pyridinyl)acetone, (4-pyridinyl)acetone, furanylacetone, pyrrolylacetone, pyrrolidinylacetone, tetrahydrofuranylacetone, cyclohexylacetone, tetralinone, cyclopropylacetone, cyclobutylacetone, cyclopentylacetone, phenyl propyl ketone, phenyl butyl ketone, phenyl ethyl ketone, 2-heptanone, 2-hexanone, 2-pentanone, 2-butanone, 2-octanone, 2-nonanone, 2-decanone, tertiary-butyl methyl ketone, isopropyl methyl ketone, methoxyacetone, ethoxyacetone, 2-ketopropanoic acid(ester), 3-ketobutanoic acid (ester).

e) Catalyst Complexes

The catalyst complex K according to the invention is preferably a ruthenium catalyst having the following general formula IV, and is as defined above

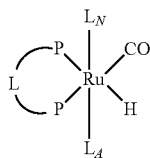

(IV)

The ligands comprised herein are explained in more detail below, wherein the following definitions do not apply only to the specific ruthenium catalyst:

e1) Phosphane Ligands (P-L-P) (Corresponding to the Above General Formula III)

Non-limiting example of useable bidentate phosphane ligands according to the invention include:

Inventive phosphane ligands according to formula III by way of example include, but are not limited to: diphenylphosphinomethane, 1,2-bis(dimethylphosphino)ethane, 1,2-bis(diisopropylphosphino)ethane, 1,2-diphenylphosphinoethane, 1,3-bis(diphenylphosphino)propane, (2,2-dimethyl-1,3-propanediyl)bis(diphenylphosphine), (2,2-dibutyl-1,3-propanediyl)bis(diphenylphosphine), bis(diphenylphosphino)butane, bis(diphenylphosphino)-9,9-dimethylxanthene, 2,3-bis(dicyclohexylphosphino)ethane, 1,1'-bis(diphenylphosphino)ferrocene, 1,1'-bis(2-diphenylphosphinoethyl)phenylphosphine, bis[2-(diphenylphosphanyl)phenyl] ether, bis(2-diphenylphosphinoethyl)phenylphosphine, bis[(2-diphenylphosphinoethyl)ethyl]amine, 1,3-bis(bis-o-methoxyphenylphosphino)propane, 1,3-bis(di-t-butylphosphinomethyl)benzene and also bis(dicyclohexylphosphinomethyl)acridine.

For the embodiments according to the invention for the enantioselective amination of the carbonyl compound, chiral phosphane ligands are used corresponding to formula III. Inventive chiral phosphane ligands according to formula III by way of example include, but are not limited to: Chiraphos (1), BINAP (13), f-Binaphane (74), and also all other phosphane ligands depicted below (1)-(86) and also enantiomers thereof.

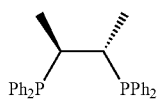

1

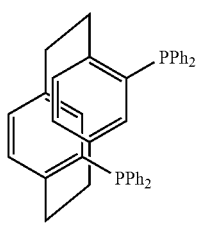

2

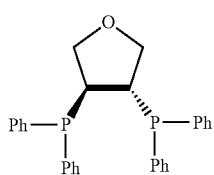

3

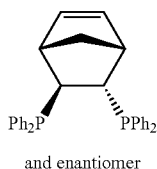

4 and enantiomer

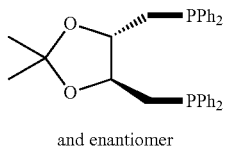

5 and enantiomer

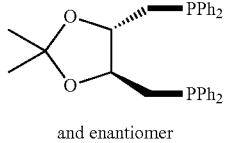

6

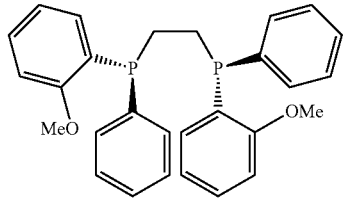

7

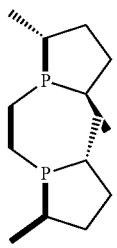

8

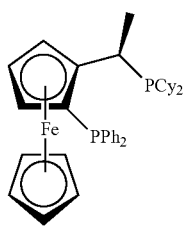

9

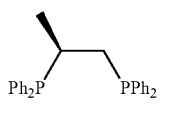

10

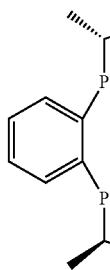

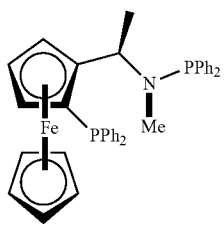
11
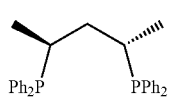
12
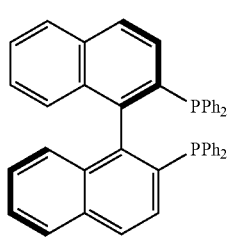
13
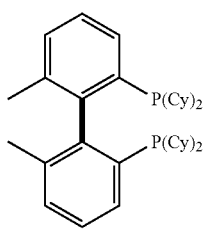
14
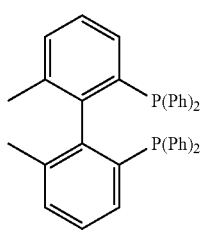
15
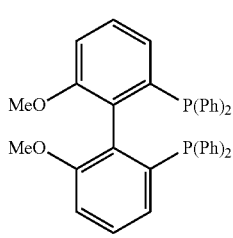
16
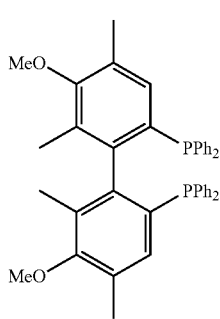
17
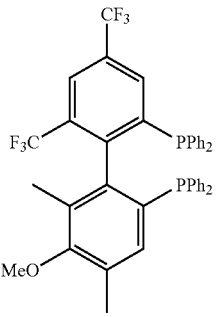
18
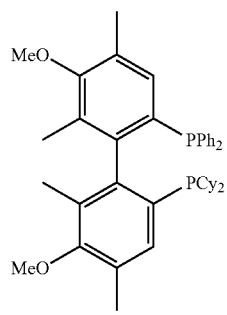
19
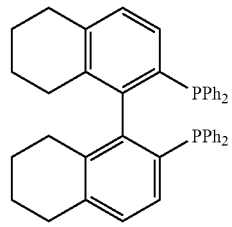
20
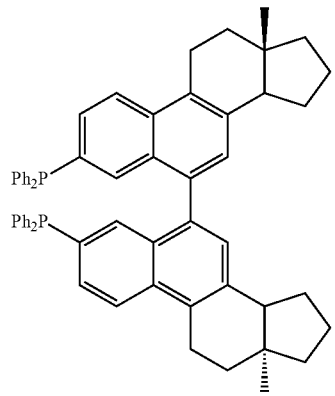
21
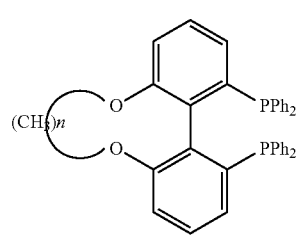
n = 1-6
22

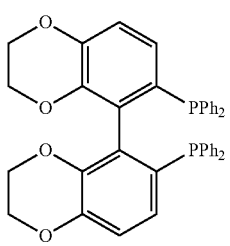
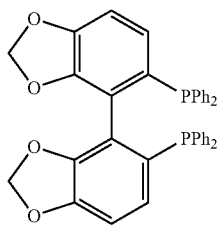
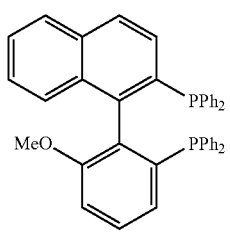
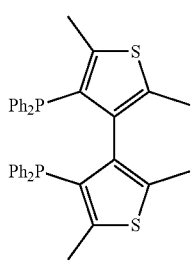
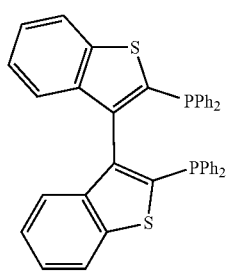
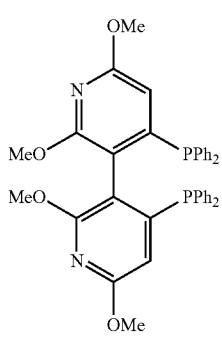
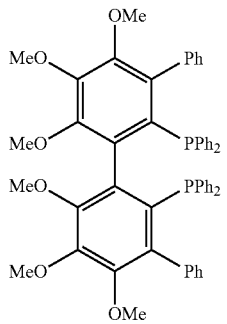
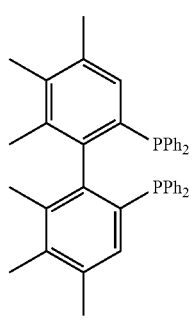
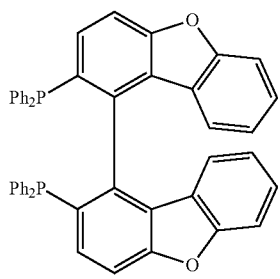
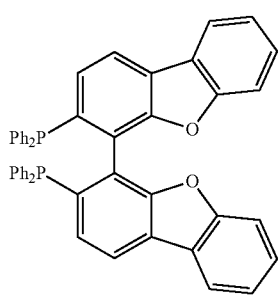
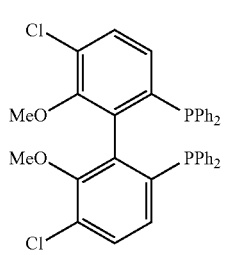

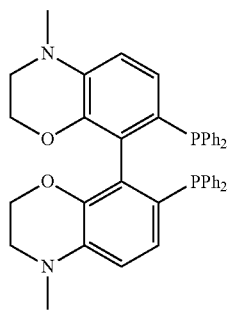
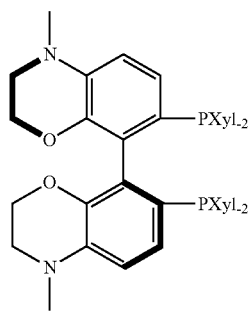
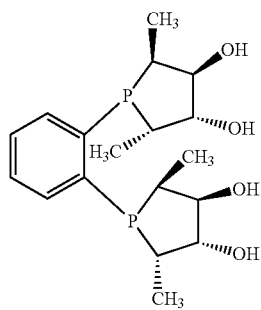
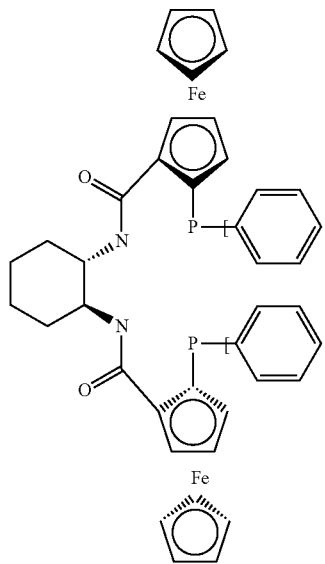
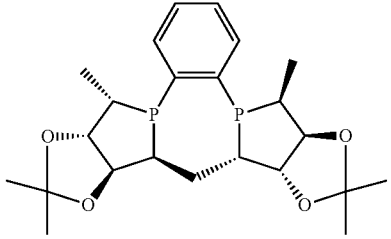
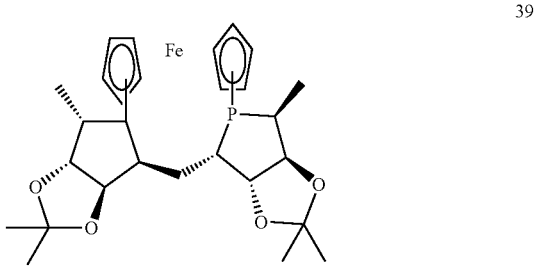
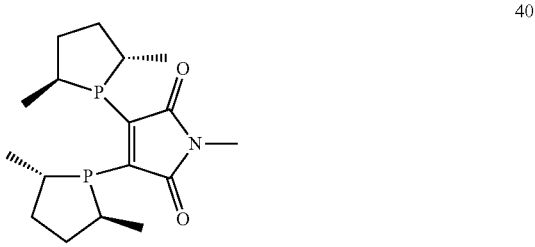
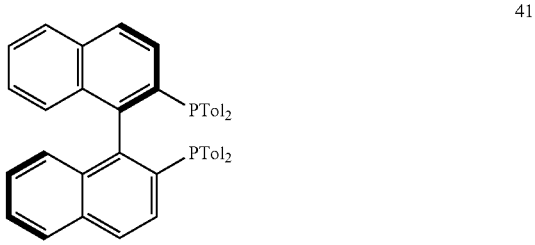
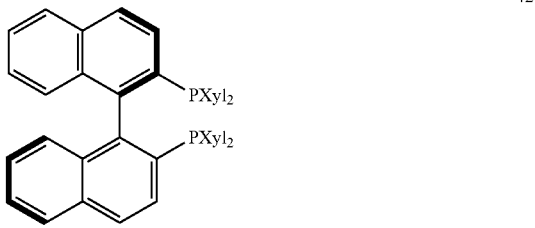
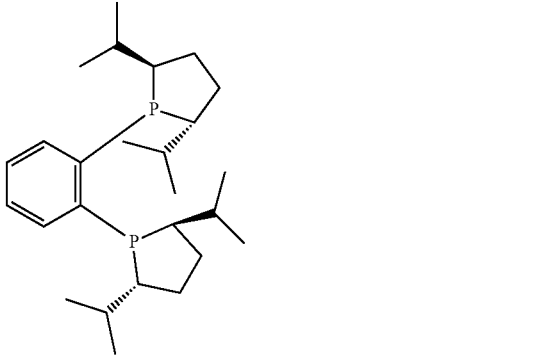

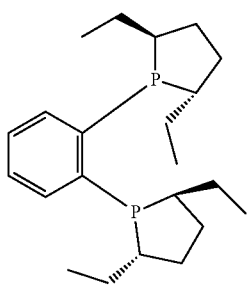
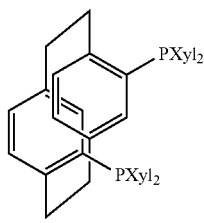
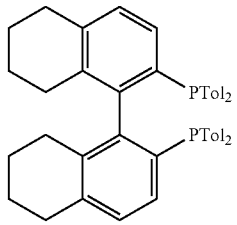
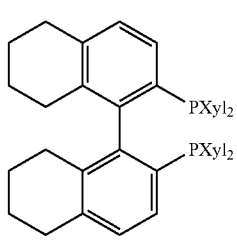
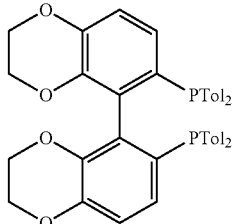
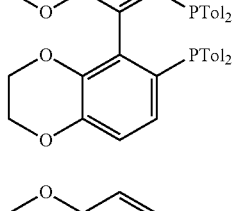
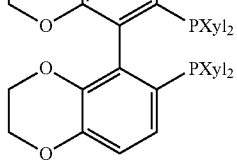
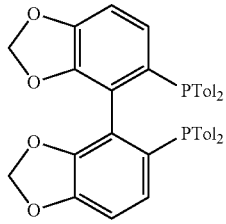

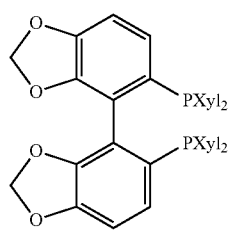
55
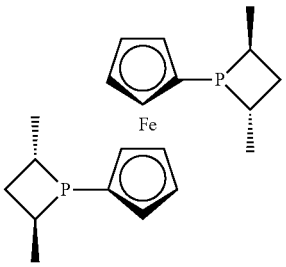
61
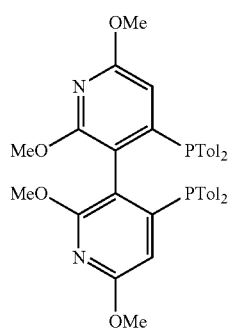
56
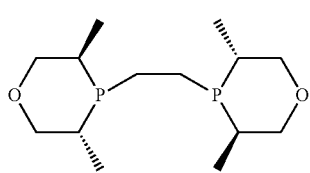
62
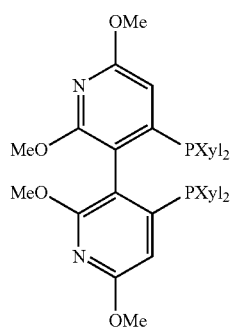
57
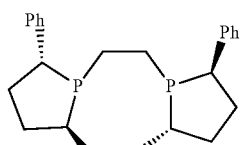
63
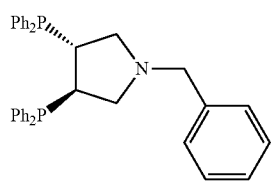
58
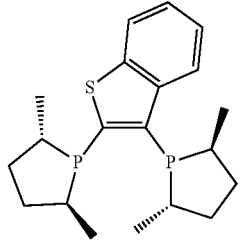
64
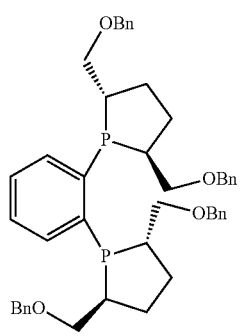
59
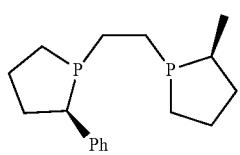
65
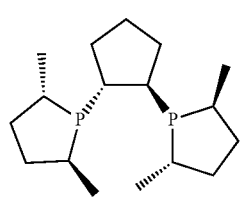
60
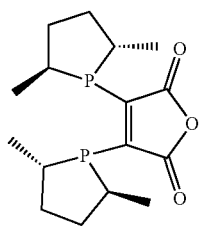
66

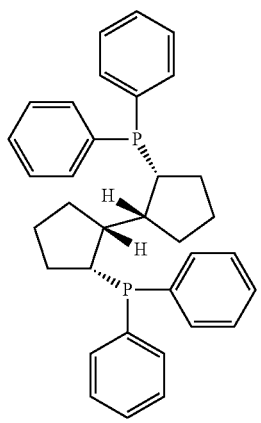
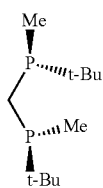
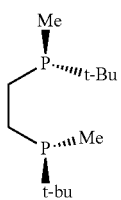
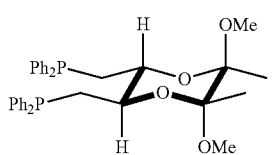
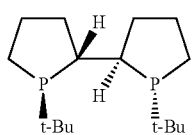
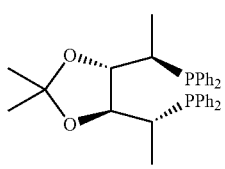
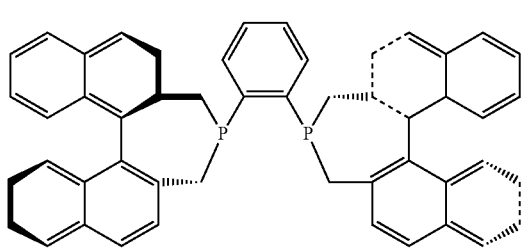
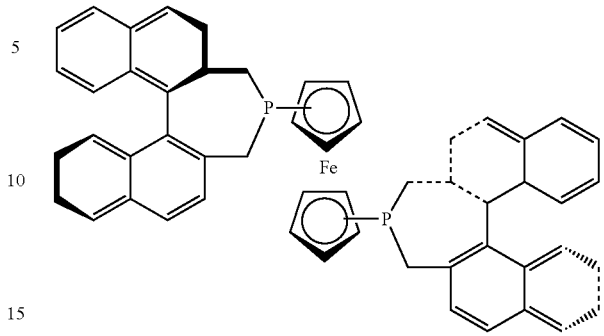
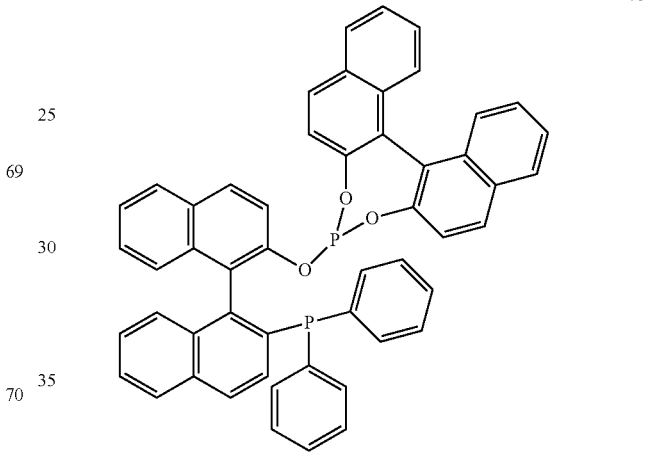
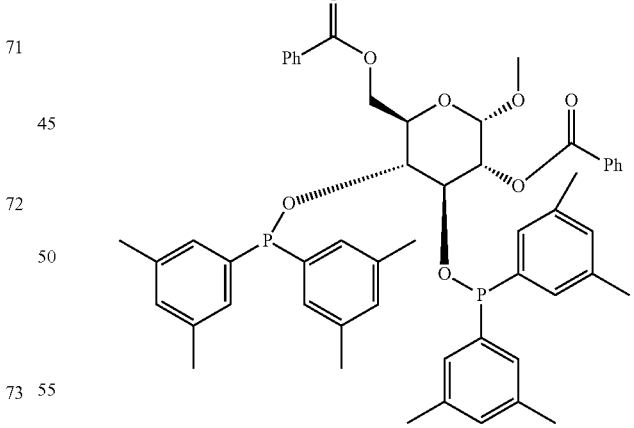
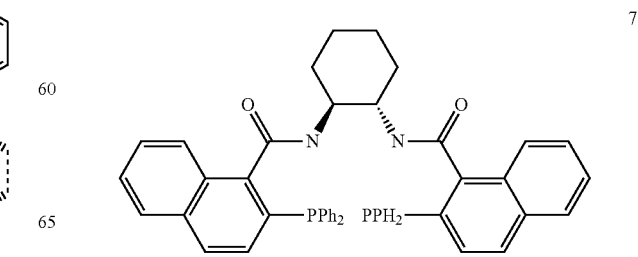

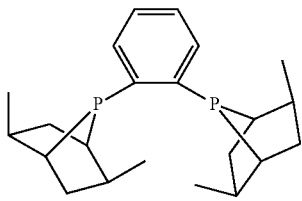

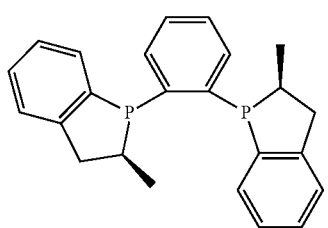

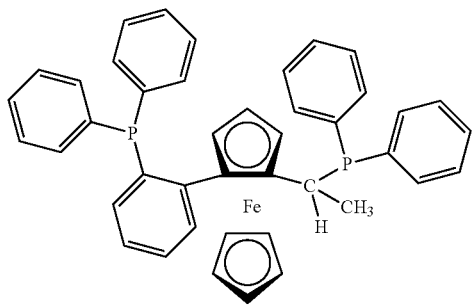

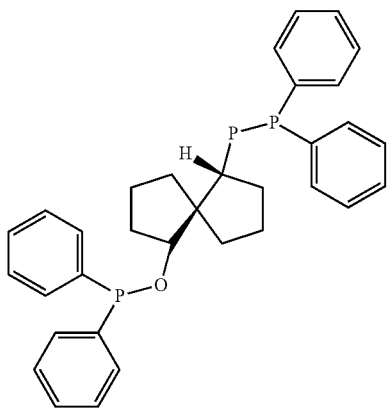

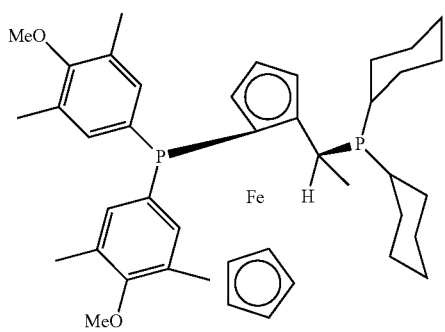

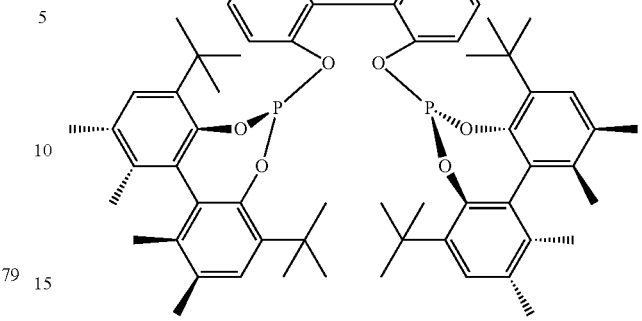

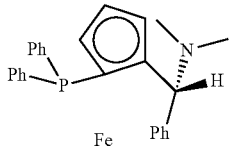

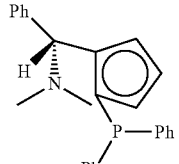

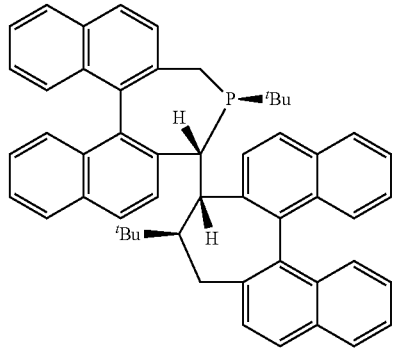

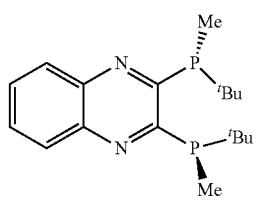

Cy represents cyclohexyl e2) Neutral Ligand $L_N$

The inventive catalyst complex according to formula IV may optionally also bear further ligands. The catalyst complex may also bear neutral ligands $L_N$, wherein said ligand is not necessary for the method according to the invention. If the catalyst complex according to formula IV bears a neutral ligand $L_N$, said ligand is preferably selected from, but not limited to, amines such as $C_1$-$C_{30}$- or particularly $C_1$-$C_6$-mono- or dialkylamines, phosphines (i.e. phosphanes) such as trialkyl- or triarylphosphanes, such as tri-$C_1$-$C_{30}$-alkyl- or tri-$C_5$-$C_{14}$-arylphosphanes, phosphites, alcohols such as aliphatic $C_1$-$C_{30}$— or particularly $C_1$-$C_6$-monoalcohols, N-heterocyclic carbenes, imines, carbonyl compounds, olefins such as $C_2$-$C_{30}$- or particularly $C_2$-$C_6$-monoolefins, alkynes such as $C_2$-$C_{30}$- or particularly $C_2$-$C_6$-monoalkynes, or nitriles such as $C_2$-$C_{30}$- or particularly $C_2$-$C_6$-monoalkylnitriles. These are particularly selected from the amines, imines, $NH_3$, triaryl- or trialkylphosphanes mentioned.

3) Anionic Ligand $L_A$

The catalyst complex may also bear an anionic ligand $L_A$, wherein said ligand is not necessary for the method according to the invention. If the catalyst complex according to formula IV bears a neutral ligand $L_N$, said ligand is preferably selected from, but not limited to, chloride, fluoride, bromide, iodide, hydride, cyanide, alkoxy, amido or hydroxyl, particularly chloride and hydride.

In a preferred embodiment, the inventive catalyst complex according to formula IV bears a neutral ligand $L_N$ and an anionic ligand Y.

In a particularly preferred embodiment, $L_N$ is a triarylphosphane such as triphenylphosphane, or $NH_3$ and $L_A$ is chloride or hydride.

The homogeneous catalyst complex according to formula IV can be generated both directly in its active form and starting from customary precursors by first adding the corresponding ligands under the reaction conditions (in situ). Non-limiting examples of customary precursors of ruthenium catalyst complexes are:

[Ru(PPh$_3$)$_3$(H)(Cl)(CO)], [Ru(PPh$_3$)$_3$(H)$_2$(CO)], [Ru(PPh$_3$)$_3$(Cl)$_2$], [Ru(PPh$_3$)$_3$(Cl)$_2$(CO)], [Ru(p-cymene)(Cl)$_2$], [Ru(benzene)Cl$_2$]$_n$, [Ru(CO)$_2$Cp]$_n$, [Ru(CO)$_3$(Cl)$_2$], [Ru(COD)(allyl)], [Ru(COD)(2-methylallyl)$_2$], [RuCl$_3$*H$_2$O], [Ru(acetylacetonate)$_3$], [Ru(DMSO)$_4$(Cl)$_2$], Ru$_3$CO$_{12}$, [Ru(cyclopentadienyl)(PPh$_3$)$_2$(Cl)], [Ru(cyclopentadienyl)(CO)$_2$(Cl)], [Ru(cyclopentadienyl)(CO)$_2$H], [Ru(cyclopentadienyl)(CO)$_2$]$_2$, [Ru(pentamethylcyclopentadienyl)(CO)$_2$(Cl)], [Ru(pentamethylcylcopentadienyl)(CO)$_2$H], [Ru(pentamethylcyclopentadienyl)(CO)$_2$]$_2$, [Ru(indenyl)(CO)$_2$(Cl)], [Ru(indenyl)(CO)$_2$(H)], [Ru(indenyl)(CO)$_2$]$_2$, ruthenocene, [Ru(binap)Cl$_2$], [Ru(bipyridine)$_2$Cl$_2$*2H$_2$O], [Ru(COD)Cl$_2$]$_2$, [Ru(pentamethylcyclopentadienyl)(COD)(Cl)], [Ru$_3$(CO)$_{12}$], [Ru(tetraphenylhydroxycyclopentadienyl)(CO)$_2$(H)], [Ru(PPh$_3$)$_4$(H)$_2$].

f) Co-catalyst

The reaction according to the invention is carried out particularly in the presence of an acid as co-catalyst. In this case, the acid may be a Bronsted or Lewis acid. The acidic co-catalyst may be present in dissolved, in partially dissolved or in undissolved form in the reaction mixture. Suitable as co-catalyst in this case are a wide variety of acidic compounds such as HCl, $H_2SO_4$, $H_3PO_4$, $HSO_3R$, HBr, HI, HF, [NH$_4$]TFA, [NH$_4$]Cl, [NH$_4$]$_2$[SO$_4$], [NH$_4$]Br, Al(OTf)$_3$, Sc(OTf)$_3$, AlCl$_3$, AlBr$_3$, Al(OR)$_3$, BR$_3$, BCl$_3$, BBr$_3$, BF$_3$, Al(NO$_3$)$_3$, NaPF$_6$, NaBF$_4$, acidic ion exchangers, TiO$_2$ (acidic), Al$_2$O$_3$(acidic), SiO$_2$, TiCl$_4$, TiBr$_4$, TiI$_4$, Ti(OR)$_4$, ZrCl$_4$, ZrBr$_4$, ZrI$_4$, ZR(OR)$_4$, H$_2$CO$_3$, CO$_2$, HCOOH, AcOH, SO$_3$, SO$_2$, or also acidic ionic liquids such as 1,3-alkylmethylimidazolium or N-alkylpyridinium salts such as 1,3-butylmethylimidazolium (BMIM) salts, where the counterion is selected, depending on the desired acidity, from e.g. MeSO$_3^-$, AlCl$_4^-$, CuCl$_2^-$, SbF$_4^-$, SbF$_6^-$, BF$_4$, PF$_6^-$, Al$_2$Cl$_7^-$, Cu$_2$Cl$_3^-$, Al$_3$Cl$_{10}^-$ or Cu$_3$Cl$_4^-$.

The amount of co-catalyst is generally 0.001 to 10% by weight, based in each case on the total liquid reaction medium.

g) Reaction Procedure

The reaction is carried out in the liquid phase generally at a temperature of 20 to 250° C. The method according to the invention is preferably carried out at temperatures in the range of 100° C. to 200° C., particularly preferably in the range of 110 to 160° C.

The reaction may be carried out generally at a total pressure of 0.1 to 20 MPa absolute, which corresponds to both the autogenous pressure of the solvent at the reaction temperature and the pressure of the ammonia and hydrogen. The method according to the invention is preferably carried out at a total pressure in the range of 0.1 to 30 MPa absolute, particularly preferably at a total pressure in the range of 1 to 10 MPa absolute.

The average reaction time is generally from 15 minutes to 100 hours, e.g. 1 to 50 or 5 to 20 hours.

With respect to the carbonyl groups to be aminated, the aminating agent (ammonia) may be used in stoichiometric, substoichiometric or superstoichiometric amounts. In a preferred embodiment, ammonia is used at a 1.5 to 250-fold, preferably at a 2 to 100-fold, particularly at a 2 to 10-fold molar excess per mole of carbonyl group to be converted in the reactant. Larger excesses of ammonia are also possible.

With respect to the carbonyl groups to be aminated, the reducing agent (hydrogen) may be used in stoichiometric, substoichiometric or superstoichiometric amounts. In a preferred embodiment, hydrogen is used at a 1.5 to 250-fold, preferably at a 2 to 100-fold, particularly at a 2 to 10-fold molar excess per mole of carbonyl group to be converted in the reactant. Larger excesses of hydrogen are also possible.

The method according to the invention may be carried out both in a solvent and without solvent. Suitable solvents are polar and non-polar solvents which may be used in pure form or in mixtures. In the method according to the invention, for example, only a non-polar or a polar solvent may be used. It is also possible to use mixtures of two or more polar solvents or mixtures of two or more non-polar solvents or mixtures of one or more polar with one or more non-polar solvents.

Suitable non-polar solvents are, for example, saturated and unsaturated hydrocarbons such as hexane, heptane, octane, cyclohexane, benzene, toluene, xylene and mesitylene, and also linear and cyclic ethers such as THF, diethyl ether, 1,4-dioxane, MTBE (tert-butyl methyl ether), diglyme and 1,2-dimethoxyethane. Preference is given to using toluene, xylenes or mesitylene.

Suitable polar solvents are, for example, water, dimethylformamide, formamide, tert-amyl alcohol and acetonitrile. Preference is given to using water. The water may be added both before the reaction, may be formed as water of reaction in the reaction, and may be added in addition to the water of reaction after the reaction.

Depending on the polarity of the product and the reactant, product and/or reactant can also be employed as solvent (in pure form or in a mixture with at least one of the abovementioned polar or non-polar solvents) for the reaction.

Ionic liquids (IL) may also optionally be used as solvent, such as the abovementioned acidic ILs.

For the reaction in the liquid phase, ammonia, hydrogen and the reactant having at least one functional group of the formula (—C=O—) are introduced into a suitable reactor, optionally together with one or more solvents, together with the catalyst complex and the co-catalyst.

The ammonia, hydrogen, reactant, optionally solvent and catalyst complex can be supplied simultaneously or separately from one another. The reaction in this case may be carried out continuously, in semi-batch mode, in batch mode, backmixed into product as solvent or not backmixed in a single pass. In a further embodiment, CO may be supplied to the reaction mixture in order to keep the catalyst in its active form.

For the method according to the invention, in principle any reactors can be used which are in principle suitable for gas/liquid reactions under the given temperature and the given pressure. Suitable standard reactors for gas/liquid and for liquid/liquid reaction systems are reported, for example, in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, Chapter 3.3 "Reactors for gas-liquid reactions". Examples include stirred tank reactors, tubular reactors or bubble column reactors.

The reaction output formed in the reaction generally comprises the corresponding reaction products (i.e. amination products and optionally resulting by-products), optionally the one or more solvents, the catalyst complex, the acidic co-catalyst and optionally unreacted reactants, ammonia and hydrogen and also the water of reaction produced. The optionally present excess ammonia, the optionally present solvent, the catalyst complex and the water of reaction are removed from the reaction output. The resulting reaction product can be further processed. The excess ammonia, the catalyst complex, the acidic co-catalyst, optionally the solvent(s) and optionally unreacted reactants may be fed back into the amination reaction.

If the amination reaction is carried out without solvent, the homogeneous catalyst complex is dissolved in the product after the reaction. This can remain in the product or be removed therefrom by a suitable method. Possibilities for the removal of the catalyst are, for example, washing out with a solvent, immiscible with the product, in which, by suitable choice of the ligands, the catalyst is more highly soluble than in the product. By means of multistage extraction, the catalyst is optionally depleted from the product. The extractant used is preferably a solvent also suitable for the target reaction such as toluene, benzene, xylenes, alkanes such as hexanes, heptanes and octanes, and acyclic or cyclic ethers such as diethyl ether and tetrahydrofuran, which may be used again for the reaction after concentration together with the extracted catalyst. It is also possible to remove the catalyst using a suitable absorber. Removal may also be achieved by the addition of water to the product phase, if the reaction is carried out in a solvent immiscible with water. If the catalyst dissolves preferentially in the solvent, it can be separated with the solvent from the aqueous product phase and optionally be reused. This can be effected by the choice of suitable ligands. It is also possible to separate the amination product from the catalyst by distillation.

If the reaction is carried out in a solvent, said solvent may be miscible with the amination product and may be removed by distillation after the reaction. Solvents may also be used having a miscibility gap with the amination products or reactants. Suitable solvents in this case include, for example, toluene, benzene, xylenes, alkanes such as hexanes, heptanes and octanes, and acyclic or cyclic ethers such as diethyl ether, tetrahydrofuran and dioxane. By means of suitable selection of the phosphane ligands, the catalyst dissolves preferentially in the solvent phase, i.e. in the phase not containing product. The phosphane ligands may also be selected such that the catalyst dissolves in the amination product. In this case, the amination product can be separated from the catalyst by distillation.

The solvent may also be miscible with the reactants and the product under the reaction conditions and only after cooling may form a second liquid phase which comprises the bulk of the catalyst. Solvents which exhibit this property include, for example, toluene, benzene, xylenes and alkanes such as hexanes, heptanes and octanes. The catalyst may then be separated together with the solvent and be re-used. In this variant, the product phase may also be admixed with water. The portion of the catalyst present in the product can subsequently be removed by suitable absorber materials such as polyacrylic acid and salts thereof, sulfonated polystyrenes and salts thereof, activated carbons, montmorillonites, bentonites and zeolites or even be left in the product.

The amination reaction can also be carried out biphasically. In the embodiment of the biphasic reaction regime, particularly suitable non-polar solvents are toluene, benzene, xylenes, alkanes such as hexanes, heptanes and octanes, in combination with lipophilic phosphane ligands on a transition metal catalyst whereby the transition metal catalyst accumulates in the non-polar phase. In this embodiment, in which the product and also the water of reaction and optionally unreacted reactants form two phases enriched with these compounds, the bulk of the catalyst can be separated from the product phase by simple phase separation and can be re-used.

If volatile by-products or unreacted reactants, or also water formed during the reaction or added after the reaction to improve extraction, are undesirable, these can be removed from the product without difficulty by distillation.

It may also be advantageous to remove the water formed during the reaction continuously from the reaction mixture. The water of reaction can be removed directly from the reaction mixture by distillation or as an azeotrope by addition of a suitable solvent (azeotroping agent) and by using a water separator or by adding water-removing auxiliaries.

The invention is illustrated by the following examples, without being limited thereto:

EXPERIMENTAL SECTION

General Details:

The gas chromatographic determinations are carried out as follows: The samples were measured after the reaction after addition of dodecane as internal standard on a Hewlett-Packard 6890 gas chromatograph, equipped with a DB-1 column (30 m×0.25 mm×1 µm). Temperatures: Initially 130° C. (5 min), 2° C./min to 160° C. and maintain three minutes, then at 50° C./min to 300° C. and maintain ten minutes.

The HPLC determinations are carried out as follows: HPLC instrument from Agilent Technologies Model 1200 Infinity equipped with a UV/Vis detector, Chiralpack IA column (0.46 cm diameter×25 cm), flow rate 1 ml/min; eluent at start 98% n-hexane and 2% 2-propanol, after 2 minutes 90% n-hexane and 10% 2-propanol and after four minutes 85% n-hexane and 15% 2-propanol.

"Inert conditions": The operations were carried out under exclusion of air and oxygen. The reactant, solvent and catalyst were weighed out in a glove box which is operated with pure argon. The operations apart from the glove box were carried out using standard Schlenk techniques and argon as inert gas.

Materials:

All phosphane ligands used and catalyst precursors are commercially available and were obtained from Sigma-Aldrich or Strem.

PREPARATION EXAMPLES

The reactions in the examples below were carried out under inert conditions in a 100 ml Parr stainless steel autoclave. All starting compounds were commercially available and were used without further purification.

Examples 1 to 5: Reductive Amination of Acetophenone—Variation of the Bidentate Phosphane Ligands

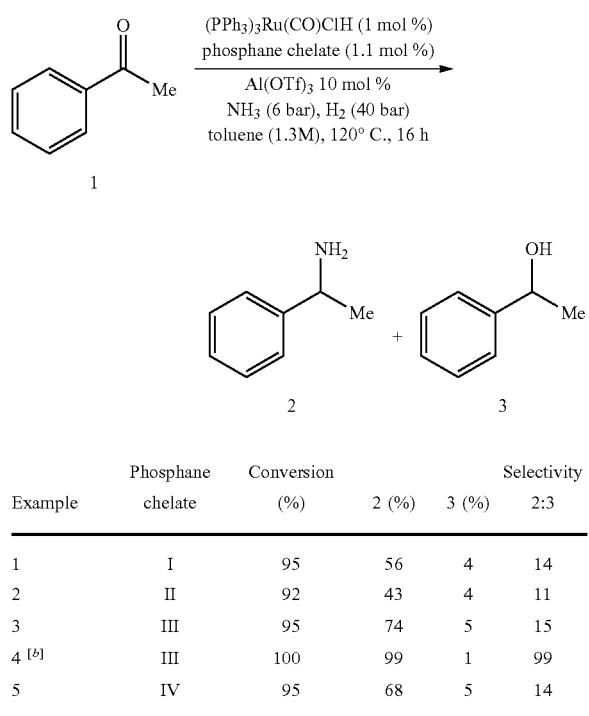

| Example | Phosphane chelate | Conversion (%) | 2 (%) | 3 (%) | Selectivity 2:3 |
|---|---|---|---|---|---|
| 1 | I | 95 | 56 | 4 | 14 |
| 2 | II | 92 | 43 | 4 | 11 |
| 3 | III | 95 | 74 | 5 | 15 |
| 4 [b] | III | 100 | 99 | 1 | 99 |
| 5 | IV | 95 | 68 | 5 | 14 |

[a] 2.97 mmol 1, Ru Catalyst (1 mol %), ligand (1.1 mol %), Al(OTf)3 (10 mol %), toluene (20 ml), 120° C., p(NH3) 6 bar, p(H2) 40 bar, 16 h. Conversion and selectivity determined by gas chromatography using dodecane as internal standard [b] 9 bar NH3.

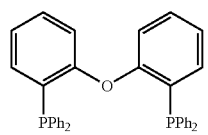

I

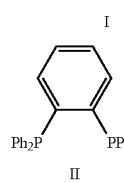

II

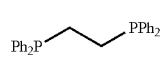

III

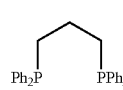

IV

Examples 1 to 5 show that, by using the inventive catalyst in combination with an acid as co-catalyst, selectivities for the primary amine of up to 99% can be obtained with complete conversion of the starting compound.

Examples 6 to 8: Reductive Amination of Acetophenone—Variation of the Ruthenium Source—CO as Essential Co-ligand

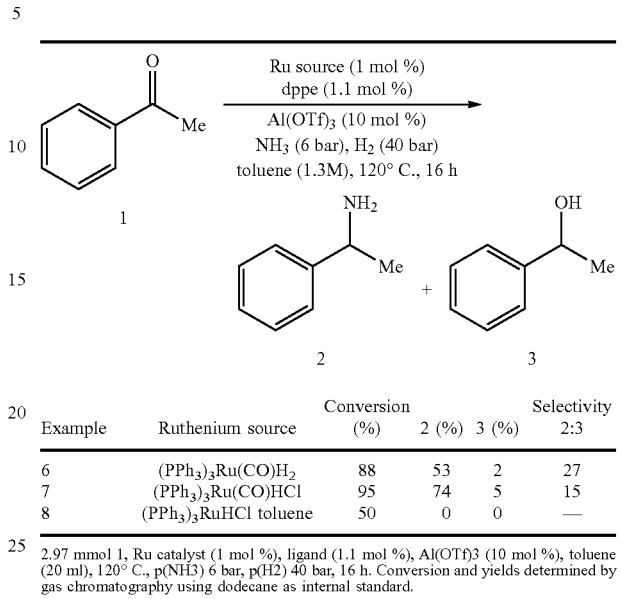

| Example | Ruthenium source | Conversion (%) | 2 (%) | 3 (%) | Selectivity 2:3 |
|---|---|---|---|---|---|
| 6 | (PPh3)3Ru(CO)H2 | 88 | 53 | 2 | 27 |
| 7 | (PPh3)3Ru(CO)HCl | 95 | 74 | 5 | 15 |
| 8 | (PPh3)3RuHCl toluene | 50 | 0 | 0 | — |

2.97 mmol 1, Ru catalyst (1 mol %), ligand (1.1 mol %), Al(OTf)3 (10 mol %), toluene (20 ml), 120° C., p(NH3) 6 bar, p(H2) 40 bar, 16 h. Conversion and yields determined by gas chromatography using dodecane as internal standard.

Examples 6 and 7 show that CO is necessary as ligand to obtain an active catalyst since no product is obtained using the CO-free ruthenium source in example 8.

Examples 9 to 16: Reductive Amination of Acetophenone—Variation of the Acidic Co-catalyst and Variation of the Bidentate Phosphane Ligands

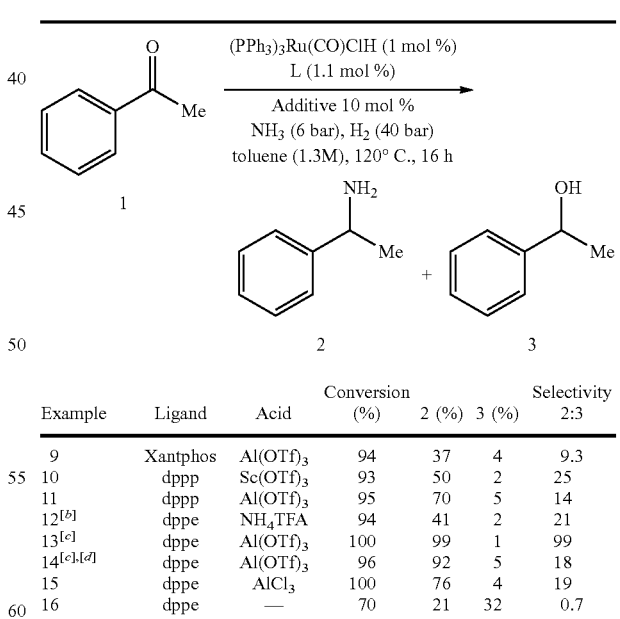

| Example | Ligand | Acid | Conversion (%) | 2 (%) | 3 (%) | Selectivity 2:3 |
|---|---|---|---|---|---|---|
| 9 | Xantphos | Al(OTf)3 | 94 | 37 | 4 | 9.3 |
| 10 | dppp | Sc(OTf)3 | 93 | 50 | 2 | 25 |
| 11 | dppp | Al(OTf)3 | 95 | 70 | 5 | 14 |
| 12[b] | dppe | NH4TFA | 94 | 41 | 2 | 21 |
| 13[c] | dppe | Al(OTf)3 | 100 | 99 | 1 | 99 |
| 14[c],[d] | dppe | Al(OTf)3 | 96 | 92 | 5 | 18 |
| 15 | dppe | AlCl3 | 100 | 76 | 4 | 19 |
| 16 | dppe | — | 70 | 21 | 32 | 0.7 |

[a] 2.97 mmol 1, Ru catalyst (1 mol %), ligand (1.1 mol %), Al(OTf)3 (10 mol %), toluene (20 ml), 120° C., p(NH3) 6 bar, p(H2) 40 bar, 16 h. Conversion and yields determined by gas chromatography using dodecane as internal standard.
[b] 1.0 eq NH4TFA.
[c] 9 bar NH3.
[d] 5 mol % f Al(OTf)3.
[e] 0.5 mol % (PPh3)3Ru(CO)HCl and 1 mol % Al(OTf)3.

Examples 8-16 show that addition of acids is necessary in the inventive method to achieve high selectivities since, without addition of acid in comparative example 16, the alcohol is formed as the main product.

Examples 17 to 29: Reductive Amination of Various Acetophenone Derivatives

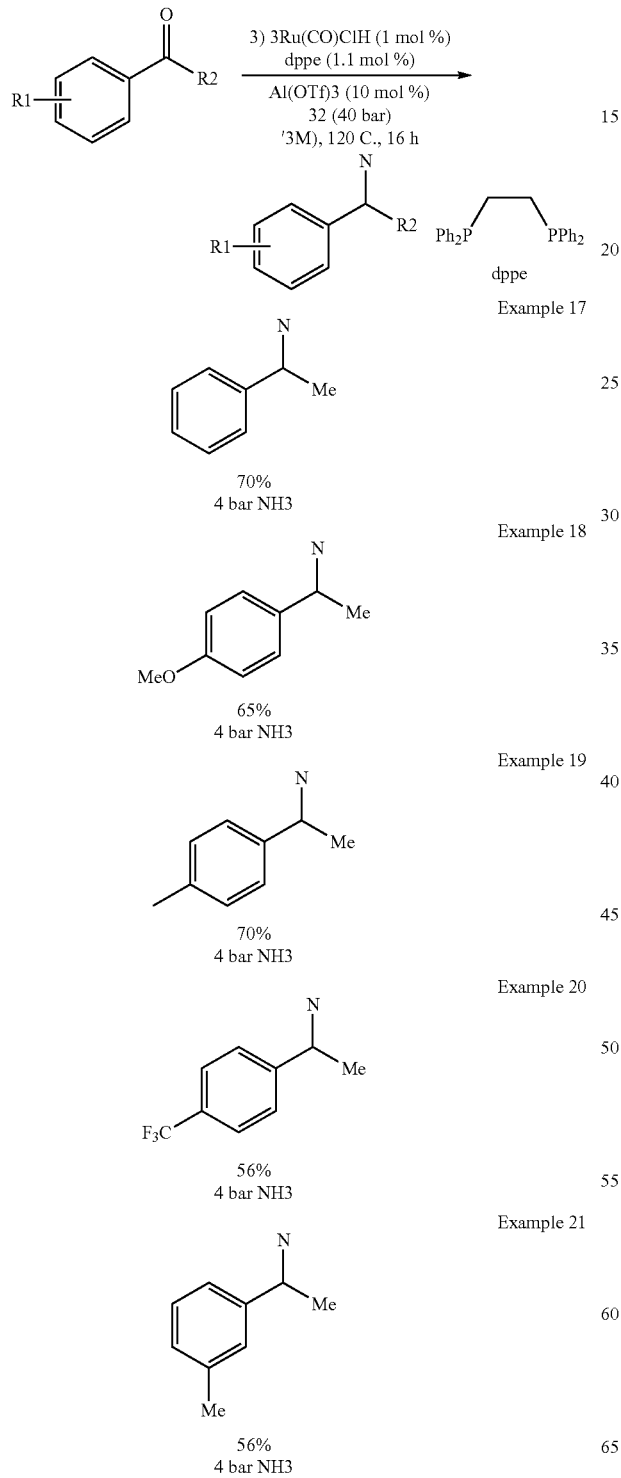

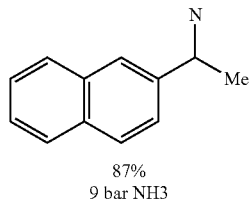

Example 22
87%
9 bar NH3

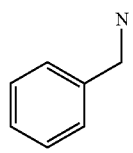

Example 23
95%
9 bar NH3

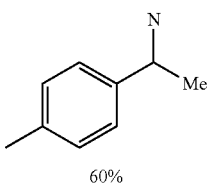

Example 24
60%
9 bar NH3

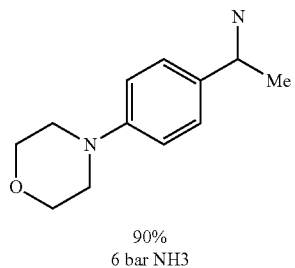

Example 25
90%
6 bar NH3

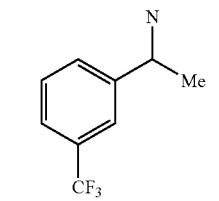

Example 26
99% (140° C.)
6 bar NH3

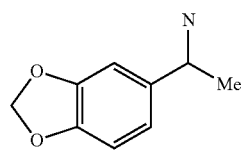

Example 27
95% (140° C.)
6 bar NH3

-continued

Example 28

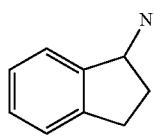

51% (140° C.)
6 bar NH3

Example 29

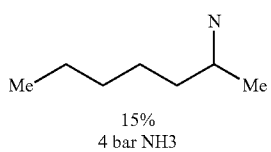

15%
4 bar NH3

Isolated yields (isolated from the reaction mixture by column chromatography)

Examples 17-29 show that various carbonyl compounds can be converted to the corresponding primary amines in good yields using the inventive method.

Examples 30 to 32: Enantioselective Reductive Amination of Acetophenone Using Various Chiral Catalysts

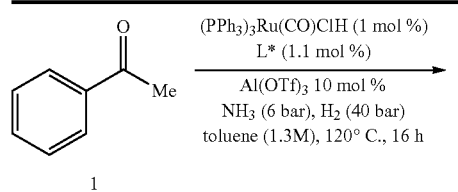

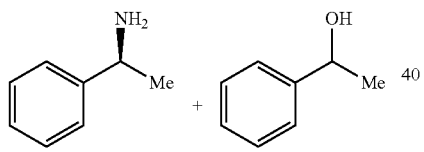

| Example | Ligand | Conversion (%) | 2 (%) | 3 (%) | Selectivity 2:3 | e.e. (%) |
|---|---|---|---|---|---|---|
| 30 | L5 | 73 | 19 | 0 | 100 | 26 |
| 31 | L6 | 73 | 10 | 10 | 1 | 53 |
| 32 | L7 | 85 | 65 | 13 | 5 | 26 |

[a] 2.97 mmol 1, Ru catalyst (1 mol %), ligand (1.1 mol %), Al(OTf)3 (10 mol %), toluene (20 ml), 120° C., p(NH3) 6 bar, p(H2) 40 bar, 16 h. Conversion and yields determined by gas chromatography using dodecane as internal standard. The enantiomeric excess (e.e) was determined by chiral HPLC after benzylation of the sample.

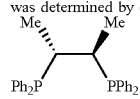

L5

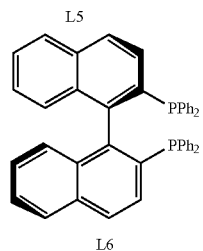

L6

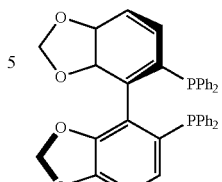

L7

Examples 30 to 32 show that the reductive amination of asymmetrical ketones can be carried out with the inventive method using chiral diphosphane ligands in such a way that a stereoisomer of the amine is preferentially formed as product.

Examples 33 to 44: Enantioselective Reductive Amination of Acetophenone Using Various Chiral Catalysts and Co-catalysts

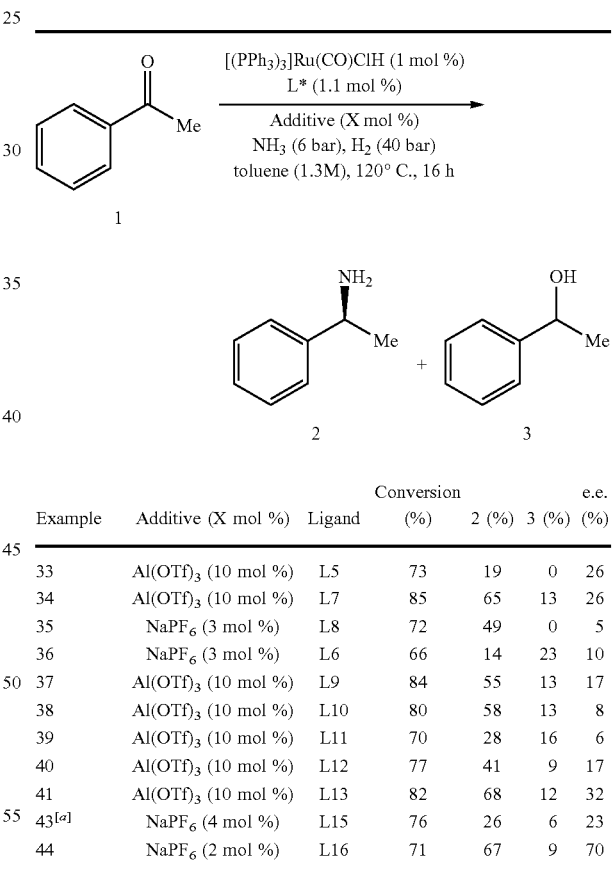

| Example | Additive (X mol %) | Ligand | Conversion (%) | 2 (%) | 3 (%) | e.e. (%) |
|---|---|---|---|---|---|---|
| 33 | Al(OTf)3 (10 mol %) | L5 | 73 | 19 | 0 | 26 |
| 34 | Al(OTf)3 (10 mol %) | L7 | 85 | 65 | 13 | 26 |
| 35 | NaPF6 (3 mol %) | L8 | 72 | 49 | 0 | 5 |
| 36 | NaPF6 (3 mol %) | L6 | 66 | 14 | 23 | 10 |
| 37 | Al(OTf)3 (10 mol %) | L9 | 84 | 55 | 13 | 17 |
| 38 | Al(OTf)3 (10 mol %) | L10 | 80 | 58 | 13 | 8 |
| 39 | Al(OTf)3 (10 mol %) | L11 | 70 | 28 | 16 | 6 |
| 40 | Al(OTf)3 (10 mol %) | L12 | 77 | 41 | 9 | 17 |
| 41 | Al(OTf)3 (10 mol %) | L13 | 82 | 68 | 12 | 32 |
| 43[a] | NaPF6 (4 mol %) | L15 | 76 | 26 | 6 | 23 |
| 44 | NaPF6 (2 mol %) | L16 | 71 | 67 | 9 | 70 |

Reaction conditions: 2.97 mmol 1, Ru catalyst (1 mol %), ligand (1.1 mol %), additive (X mol %), toluene (20 ml), 120° C., p(NH3) 6 bar, p(H2) 40 bar, 16 h. Conversion and yields determined by gas chromatography using dodecane as internal standard. The enantiomeric excess (e.e) was determined by chiral HPLC after benzylation of the sample.
[a] 2 mol % Ru complex and 2.2 mol % ligand.

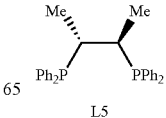

L5

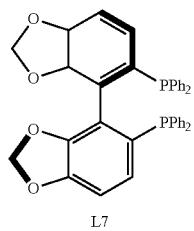

L7

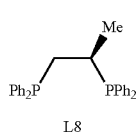

L8

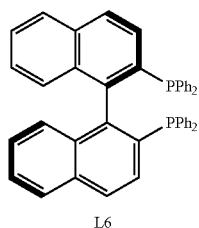

L6

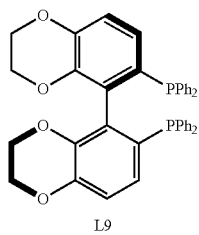

L9

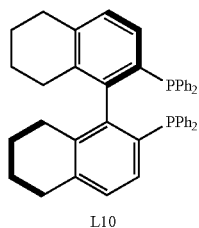

L10

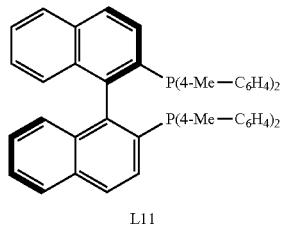

L11

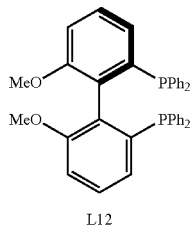

L12

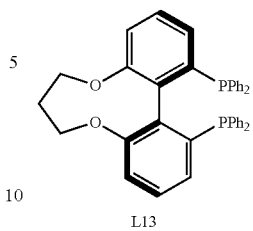

L13

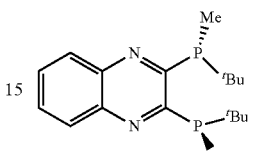

L15

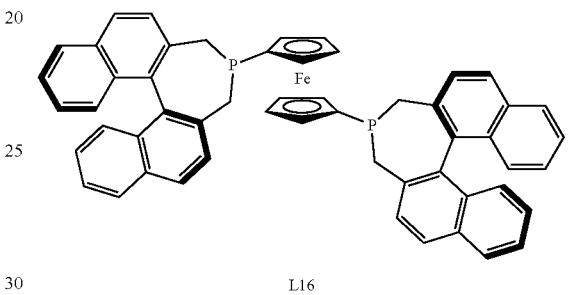

L16

Examples 45 to 48: Enantioselective Reductive Amination of Acetophenone Using Various Co-catalysts

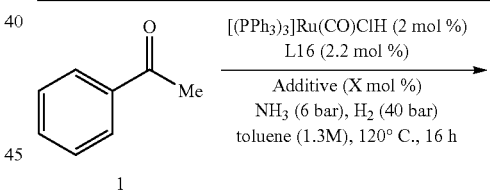

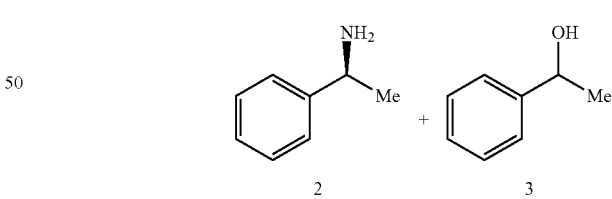

| Example | Solvent | Additive (X mol %) | Conversion (%) | 2 (%) | 3 (%) | e.e. (%) |
|---|---|---|---|---|---|---|
| 45 | PhCF$_3$ | NaPF$_6$ (4 mol %) | 83 | 78 | 0 | 54 |
| 46 | PhOMe | NaPF$_6$ (4 mol %) | 62 | 51 | 3 | 50 |
| 47 | PhCl | NaPF$_6$ (4 mol %) | 98 | 93 | 1 | 63 |
| 48 | PhCl | Al(OTf)$_3$ (10 mol %) | 85 | 77 | 0 | 66 |

Reaction conditions: 2.97 mmol 1, Ru catalyst (2 mol %), ligand (2.2 mol %), additive (X mol %), toluene (20 ml), 120° C., p(NH$_3$) 6 bar, p(H$_2$) 40 bar, 16 h. Conversion and yields determined by gas chromatography using dodecane as internal standard. The enantiomeric excess (e.e) was determined by chiral HPLC after benzylation of the sample.
[a] 2 mol % Ru complex and 2.2 mol % ligand.

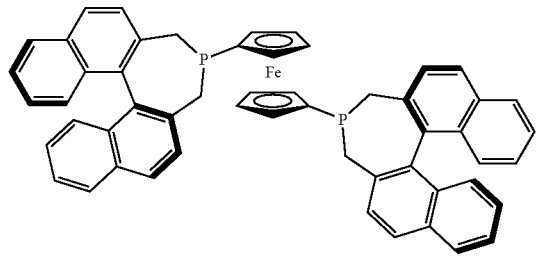

L16

Examples 33 to 48 show that the reductive amination of asymmetrical ketones can be carried out with the inventive method using chiral diphosphane ligands in such a way that a stereoisomer of the amine is preferentially formed as product.

The disclosure of the publications cited herein is explicitly incorporated by reference.

The invention claimed is:

1. A method for the reductive amination of a carbonyl compound, comprising one or more carbonyl groups amenable to reductive amination, characterized in that the reaction is carried out in the presence of a homogeneously dissolved catalyst K and an acid as co-catalyst, in which the catalyst K is a ruthenium catalyst, comprising, a bidentate phosphane ligand, a carbonyl ligand, a hydride ligand and optionally a neutral ligand.

2. The method according to claim 1, wherein the bidentate phosphane ligand has the following formula III:

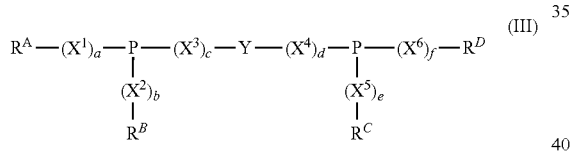

where a, b, c, d, e and f are mutually independently 0 or 1, $X^1$, $X^2$, $X^3$, $X^4$, $X^5$ and $X^6$ are mutually independently alkylene, arylene, O, S, —(C=O)—$NE^7$-metallocenyl, metallocenyl-$NE^7$-(C=O)—, —(C=O)—$NE^7$-, —$NE^7$-(C=O)— or $NE^8$, where $E^8$ is H or an alkyl, cycloalkyl, heterocyclyl, aryl or a hetaryl residue, and $E^7$ is H or an alkyl residue; wherein said residues and the metallocenyl, alkylene or arylene groups are each independently optionally mono- or polysubstituted, and wherein the substituents are mutually independently selected from alkyl, cycloalkyl, heterocyclyl, aryl, hetaryl, alkoxy, cycloalkoxy, heterocycloalkoxy, arylloxy, hetaryloxy, hydroxyl, mer-capto, polyalkylene oxide, polyalkylenimine, COOH, carboxylate, $SO_3H$, sulfonate, halogen, nitro, formyl, acyl, cyano, $NE^1E^2$, and $NE^1E^2E^{3+}X^-$, where $E^1E^2$ and $E^3$ are each identical or different residues selected from hydrogen, alkyl, cycloalkyl, or aryl and $X^-$ is an anion equivalent, Y is a carbon atom-containing bridging group, and $R^A$, $R^B$, $R^C$ and $R^D$ are residues mutually independently selected from alkyl, cycloalkyl, heterocycloalkyl, aryl or hetaryl, wherein said residues are mutually independently optionally mono- or polysubstituted, wherein the substituents are mutually independently selected from alkyl, cycloalkyl, heterocyclyl, aryl, hetaryl, alkoxy, cycloalkoxy, heterocycloalkoxy, aryloxy, hetaryloxy, hydroxyl, mercapto, polyalkylene oxide, polyalkylenimine, COOH, carboxylate, $SO_3H$, sulfonate, halogen, nitro, formyl, acyl, cyano, $NE^1E^2$, and $NE^1E^2E^{3+}X-$, where $E^1$, $E^2$ and $E^3$ are each identical or different residues selected from hydrogen, alkyl, cycloalkyl, or aryl and $X^-$ is an anion equivalent;

or $R^A$ and $R^B$ and/or $R^C$ and $R^D$ together with the phosphorus atom and, if present, the groups $X^1$, $X^2$, $X^5$ and $X^6$ to which they are bound, are a 4- to 8-membered heterocycle or heterobicycle, which is optionally additionally fused to cycloalkyl, heterocyclyl, aryl or hetaryl, wherein the heterocycle or heterobicycle and, if present, the fused groups, are mutually independently optionally substituted, wherein the substituents are selected from alkyl, cycloalkyl, heterocyclyl, aryl, hetaryl, hydroxyl, mercapto, polyalkylene oxide, polyalkylenimine, alkoxy, halogen, COOH, carboxylate, $SO_3H$, sulfonate, $NE^4E^5$, $NE^4E^5E^{6+}X^-$, nitro, alkoxycarbonyl, formyl, acyl and cyano, where $E^4$, $E^5$ and $E^6$ are each identical or different residues selected from hydrogen, alkyl, cycloalkyl and aryl and $X^-$ is an anion equivalent;

or one of the residues $R^A$ and $R^B$ and/or one of the residues $R^C$ and $R^D$ together with the phosphorus atom and, if present, the groups $X^1$, $X^2$, $X^5$ and $X^6$ to which they are bound, and together with a bridging group atom of the bridging group Y, are a 5- to 8-membered heterocycle, which is optionally additionally fused to cycloalkyl, heterocycloalkyl, aryl or hetaryl, wherein the heterocycle and, if present, the fused groups, are in addition mutually independently optionally substituted, wherein the substituents are selected from the group consisting of alkyl, cycloalkyl, heterocyclyl, aryl, hetaryl, hydroxyl, mercapto, polyalkylene oxide, polyalkylenimine, alkoxy, halogen, COOH, carboxylate, $SO_3H$, sulfonate, $NE^4E^5$, $NE^4E^5E^{6+}X^-$, nitro, alkoxycarbonyl, formyl, acyl and cyano, where $E^4$, $E^5$ and $E^6$ are each identical or different residues selected from hydrogen, alkyl, cycloalkyl and aryl and $X^-$ is an anion equivalent.

3. The method according to claim 2, wherein the bidentate phosphane ligand is selected from compounds of the formula III, where $X^1$, $X^2$, $X^3$, $X^4$, $X^5$ and $X^6$ are mutually independently optionally substituted $C_1$-$C_6$-alkylene, O, —(C=O)—$NE^7$-ferrocenyl, ferrocenyl-$NE^7$-(C=O)—, —(C=O)—$NE^7$- or —$NE^7$-(C=O)—, where $E^7$ is as defined above;

Y, a, b, c, d, e and f are as defined above;

$R^A$, $R^B$, $R^C$ and $R^D$ are residues mutually independently selected from $C_1$-$C_{30}$-alkyl, $C_4$-$C_{10}$-cycloalkyl, $C_3$-$C_{10}$-heterocyclyl, $C_5$-$C_{14}$-aryl or $C_5$-$C_{30}$-hetaryl, wherein said residues are mutually independently optionally mono- or polysubstituted, wherein the substituents are mutually independently selected from $C_1$-$C_{10}$-alkyl, $C_4$-$C_{10}$-cycloalkyl, $C_3$-$C_{10}$-heterocycloalkyl, $C_5$-$C_{14}$-aryl, $C_5$-$C_{30}$-hetaryl, $C_1$-$C_{10}$-alkoxy, $C_3$-$C_{10}$-cycloalkoxy, $C_3$-$C_{10}$-heterocycloalkoxy, $C_5$-$C_{14}$-aryloxy, $C_5$-$C_{30}$-hetaryloxy, hydroxyl, mercapto, poly-$C_2$-$C_6$-alkylene oxide, poly-$C_2$-$C_6$-alkylenimine, COOH, carboxylate, $SO_3H$, sulfonate, halogen, nitro, formyl, $C_1$-$C_{10}$-acyl, cyano, $NE^1E^2$, and $NE^1E^2E^{3+}X^-$, where $E^1$, $E^2$ and $E^3$ are each identical or different residues selected from hydrogen, $C_1$-$C_{10}$-alkyl, $C_3$-$C_{10}$-cycloalkyl, or $C_5$-$C_{10}$-aryl and $X^{31}$ is an anion equivalent;

or $R^A$ and $R^B$ and/or $R^C$ and $R^D$ together with the phosphorus atom and, if present, the groups $X^1$, $X^2$, $X^5$ and $X^6$ to which they are bound, are a 4- to 8-membered heterocycle or heterobicycle, which is optionally additionally fused to $C_4$-$C_{10}$-cycloalkyl, $C_3$-$C_{10}$-heterocycloalkyl, $C_5$-$C_{14}$-aryl or $C_5$-$C_{30}$-hetaryl, wherein the heterocycle or heterobicycle and, if present, the fused groups, are mutually independently optionally substituted, wherein the substituents are selected from $C_1$-$C_{10}$-alkyl, $C_3$-$C_{10}$-cycloalkyl, $C_3$-$C_{10}$-heterocycloalkyl, $C_5$-$C_{14}$-aryl, $C_5$-$C_{30}$-hetaryl, hydroxyl, mercapto, poly-$C_2$-$C_6$-alkylene oxide, poly-$C_2$-$C_6$-alkylenimine, $C_1$-$C_{10}$-alkoxy, halogen, COOH, carboxylate, $SO_3H$, sulfonate, $NE^4E^5$, $NE^4E^5E^{6+}X^{31}$, nitro, $C_1$-$C_{10}$-alkoxycarbonyl, formyl, $C_1$-$C_{10}$-acyl and cyano, where $E^4$, $E^5$ and $E^6$ are each identical or different residues selected from hydrogen, $C_1$-$C_{10}$-alkyl, $C_3$-$C_{10}$-cycloalkyl and $C_5$-$C_{14}$-aryl and $X^-$ is an anion equivalent;

or one of the residues $R^A$ and $R^B$ and/or one of the residues $R^C$ and $R^D$ together with the phosphorus atom and, if present, the groups $X^1$, $X^2$, $X^5$ and $X^6$ to which they are bound, and together with a bridging group atom of the bridging group Y, are a 5- to 8-membered heterocycle, which is optionally additionally fused to $C_3$-$C_{10}$-cycloalkyl, $C_3$-$C_{10}$-heterocycloalkyl, $C_5$-$C_{14}$-aryl or $C_5$-$C_{30}$-hetaryl, wherein the heterocycle and, if present, the fused groups, are in addition mutually independently optionally substituted, wherein the substituents are selected from $C_1$-$C_{10}$-alkyl, $C_3$-$C_{10}$-cycloalkyl, $C_3$-$C_{10}$-heterocycloalkyl, $C_5$-$C_{14}$-aryl, $C_5$-$C_{30}$-hetaryl, hydroxyl, mercapto, poly-$C_2$-$C_6$-alkylene oxide, poly-$C_2$-$C_6$-alkylenimine, $C_1$-$C_{10}$-alkoxy, halogen, COOH, carboxylate, $SO_3H$, sulfonate, $NE^4E^5$, $NE^4E^5E^{6+}X^-$, nitro, $C_1$-$C_{10}$-alkoxycarbonyl, formyl, $C_1$-$C_{10}$-acyl and cyano, where $E^4$, $E^5$ and $E^6$ are each identical or different residues selected from hydrogen, $C_1$-$C_{10}$-alkyl, $C_3$-$C_{10}$-cycloalkyl and $C_5$-$C_{14}$-aryl and $X^-$ is an anion equivalent.

4. The method according to claim 1, wherein the group Y in the bidentate phosphane ligand of the general formula III is a bridging group selected from the group consisting of:
straight-chain or branched alkylene,
straight-chain or branched alkenylene,
cycloalkylene optionally comprising at least one ring heteroatom selected from the group consisting of N, O and S,
cycloalkenylene optionally comprising at least one ring heteroatom selected from the group consisting of N, O and S,
bi-, tri- and tetracyclic bridging groups;
arylene,
heteroarylene comprising at least one ring heteroatom selected from the group consisting of N, O and S,
heteroalkylene comprising at least one chain heteroatom selected from the group consisting of N, O and S,
heteroalkenylene comprising at least one chain heteroatom selected from the group consisting of N, O and S,
polycyclic bridging groups comprising at least two mutually bound aromatic, heteroaromatic, carbocyclic or heterocyclic, 4- to 8-membered rings; and
metallocene bridging groups comprising at least one metallocene group of the formula

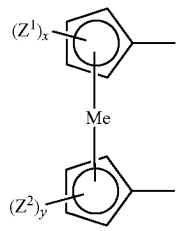

where Me is a metal atom, wherein the P atoms of the phosphane ligand are bonded directly or via one of the groups $X^3$ or $X^4$ to the same or two different Cp rings of the metallocene, x and y are mutually independently 0, 1, 2, 3 or 4 and $Z^1$ and $Z^2$ are mutually independently H, optionally mono- or polysubstituted alkyl or optionally mono- or polysubstituted aryl.

5. The method according to claim 1, wherein the group Y in the bidentate phosphane ligand of the general formula III is a polycyclic bridging group selected from groups of the formulae III.a to III.k

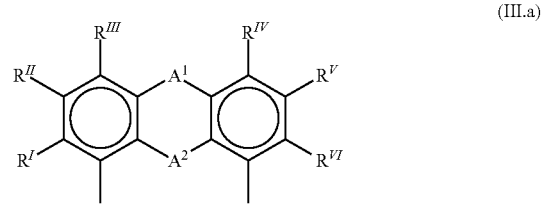

(III.a)

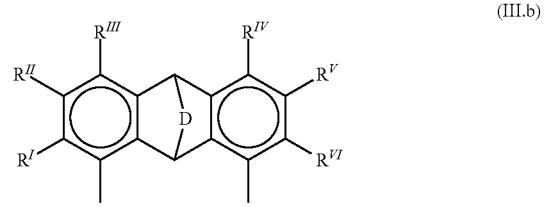

(III.b)

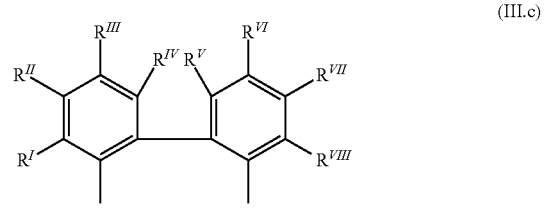

(III.c)

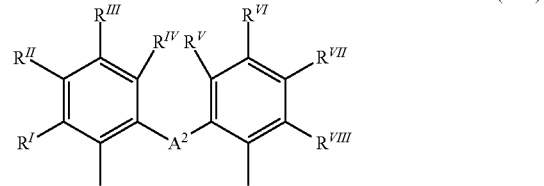

(III.d)

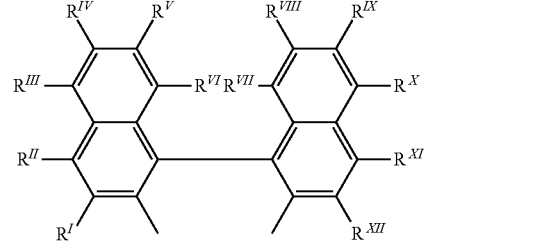

(III.e)

-continued

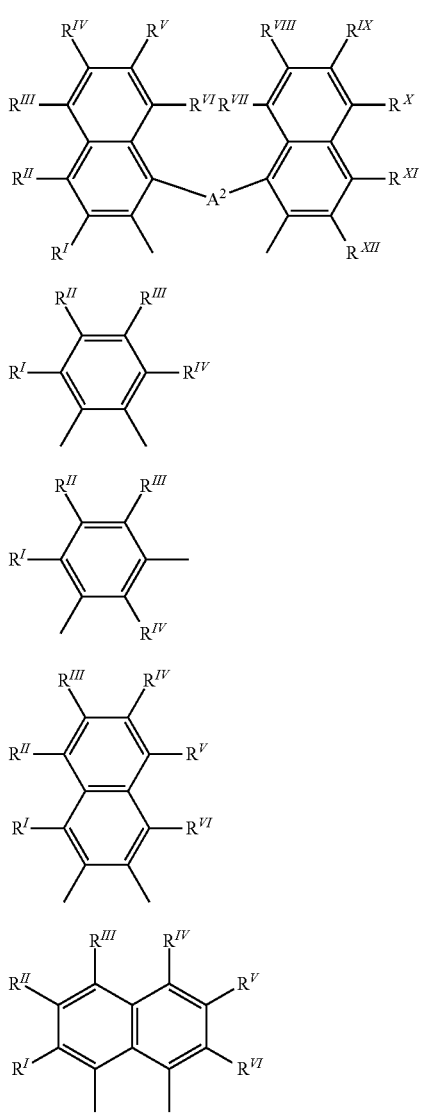

where
R$^I$, R$^{II}$, R$^{III}$, R$^{IV}$, R$^V$, R$^{VI}$, R$^{VII}$, R$^{VIII}$, R$^{IX}$, R$^X$, R$^{XI}$ and R$^{XIII}$ are mutually independently hydrogen, alkyl, cycloalkyl, heterocycloalkyl, aryl, hetaryl, hydroxyl, mercap-to, polyalkylene oxide, polyalkylenimine, alkoxy, halogen, SO$_3$H, sulfonate, NE$^9$E$^{10}$, alkylene-NE$^9$E$^{10}$, trifluoromethyl, nitro, alkoxycarbonyl, carboxyl, formyl, acyl or cyano, where E$^9$ and E$^{10}$ are each identical or different resi-dues selected from hydrogen, alkyl, cycloalkyl and aryl,
or
in each case two adjacent residues R$^I$, R$^{II}$, R$^{III}$, R$^{IV}$, R$^V$, R$^{VI}$, R$^{VII}$, R$^{VIII}$, R$^{IX}$, R$^X$, R$^{XI}$ and R$^{XII}$, together with the carbon atoms to which they are bound, form a 4- to 7-membered carbocyclic or heterocyclic, aromatic or non-aromatic ring, which in turn may optionally be fused to a mono- or polycyclic carbocyclic or heterocyclic, aromatic or non-aromatic ring, wherein said ring system is optionally substituted, wherein the substituents are selected from alkyl, cycloalkyl, heterocyclyl, aryl, hetaryl, hydroxyl, mercapto, polyalkylene oxide, polyalkylenimine, alkoxy, halogen, COOH, carboxy-late, SO$_3$H, sulfonate, NE$^4$E$^5$, NE$^4$E$^5$E$^{6+}$X$^-$, nitro, alkoxycarbonyl, formyl, acyl and cyano, where E$^4$, E$^5$ and E$^6$ are each identical or different residues selected from hydrogen, alkyl, cycloalkyl and aryl and X$^-$ is an anion equivalent;
where the two adjacent residues from R$^I$, R$^{II}$, R$^{III}$, R$^{IV}$, R$^V$, R$^{VI}$, R$^{VII}$, R$^{VIII}$, R$^{IX}$, R$^X$, R$^{XI}$ or R$^{XII}$ may be bound to carbon atoms of the same aromatic ring or to carbon atoms of two aromatic rings that are different from one another;
A$^1$ is a bond, NH, NR$^{11}$, O S, CR$^{11}$ or CR$^{11}$R$^{12}$, where R$^{11}$ and R$^{12}$ are mutually independently selected from H, alkyl and aryl;
A$^2$ is an NH, N, O or S,
D is a divalent bridging group of the general formula

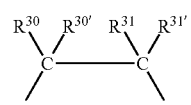

in which
R$^{30}$, R$^{30'}$, R$^{31}$ and R$^{31'}$ are mutually independently hydrogen, alkyl, cycloalkyl, aryl, halogen, trifluoromethyl, carboxyl, carboxylate or cyano,
where R$^{30'}$ together with R$^{31'}$ can also be the second bond of a double bond between the two carbon atoms to which R$^{30'}$ and R$^{31'}$ are bound, and/or R$^{30}$ and R$^{31}$ together with the carbon atoms to which they are bound can also be a 4- to 8-membered carbocycle or heterocycle, which in addition is optionally singly, doubly or triply fused with cycloalkyl, heterocycloalkyl, aryl or hetaryl, wherein the carbocycle or heterocycle and, if present, the fused groups may each mutually independently bear one, two, three or four sub-stituents selected from alkyl, cycloalkyl, heterocycloalkyl, aryl, hetaryl, COOR$^e$, COO$^-$M$^+$, SO$_3$R$^e$, SO$_3$$^-$M$^+$, NE$^{11}$E$^{12}$, alkylene-NE$^{11}$E$^{12}$, NE$^{11}$E$^{12}$E$^{13+}$X$^-$, alkylene-NE$^{11}$E$^{12}$E$^{13+}$X$^{31}$, OR$^e$, SR$^e$, (CHR$^f$CH$_2$O)$_y$R$^e$, (CH$_2$N(E$^{11}$))$_y$R$^e$, (CH$_2$CH$_2$N(E$^{11}$))$_y$R$^e$, halogen, trifluoromethyl, nitro, formyl, acyl or cyano, where
R$^e$, E$^{11}$, E$^{12}$ and E$^{13}$ are each identical or different residues selected from hydrogen, alkyl, cycloalkyl or aryl,
R$^f$ is hydrogen, methyl or ethyl,
M$^+$ is a cation equivalent,
X$^-$ is an anion equivalent, and
y is an integer from 1 to 120.

6. The method according to claim 1, wherein the group Y in the bidentate phosphane ligand of the general formula III is a bridging group selected from polycyclic groups III.m to III.o

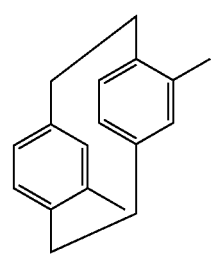

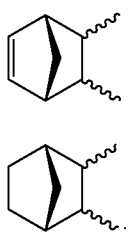

(III.n)

(III.o)

7. The method according to claim 1, wherein the group Y in the bidentate phosphane ligand of the general formula III is a bridging group selected from the heterocyclic groups V.a to V.h

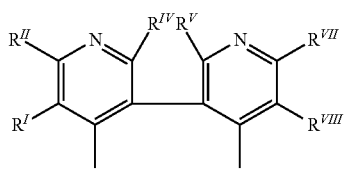

(V.a)

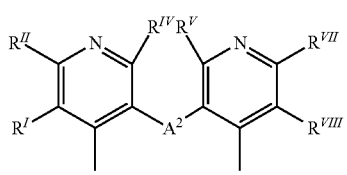

(V.b)

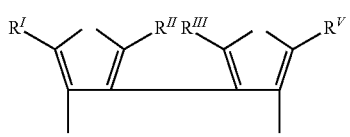

(V.c)

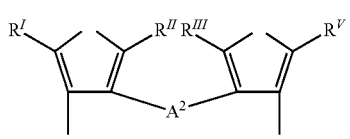

(V.d)

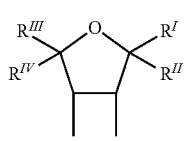

(V.e)

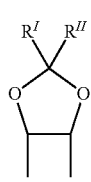

(V.f)

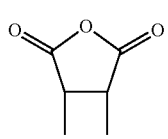

(V.g)

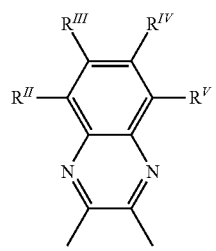

(V.h)

where the residues $R^I$ to $R^{VIII}$ are mutually independently selected from hydrogen, alkyl, cycloalkyl, heterocycloalkyl, aryl, hetaryl, hydroxyl, mercapto, polyalkylene oxide, polyalkylenimine, alkoxy, halogen, $SO_3H$, sulfonate, $NE^9E^{10}$, alkylene-$NE^9E^{10}$, trifluoromethyl, nitro, alkoxycarbonyl, carboxyl, formyl, acyl or cyano, where $E^9$ and $E^{10}$ are each identical or different residues selected from hydrogen, alkyl, cycloalkyl and aryl; and $A^2$ is an NH-11 group, N, O or S.

8. The method according to claim 1, wherein the two phosphane end groups in the bidentate phosphane ligand of the general formula III are mutually independently selected from groups of the formulae VI.a to VI.k

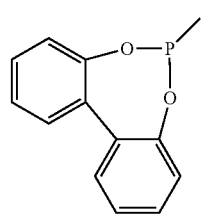

(VI.a)

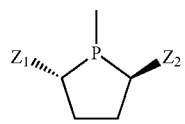

(VI.b)

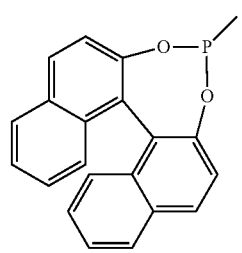

(VI.c)

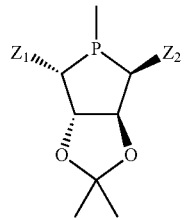

(VI.d)

-continued

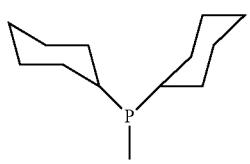
(VI.e)

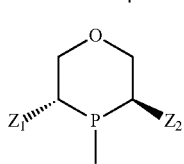
(VI.f)

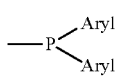
(VI.g)

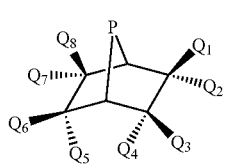
(VI.h)

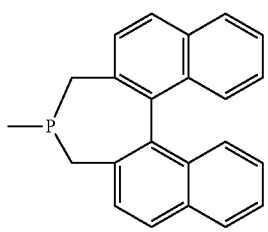
(VI.k)

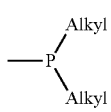
(VI.i)

where
aryl is phenyl, optionally mono- or polysubstituted, wherein the substituents are selected from alkyl or alkoxy $Z_1$ and $Z_2$ are mutually independently selected from alkyl, alkoxy, alkoxyalkyl, aryl or hetaryl and $Q_1$ to $Q_8$ are mutually independently H or alkyl.

9. The method according to claim 1, wherein the acid co-catalyst is a Lewis acid.

10. The method according to claim 1, wherein the acid co-catalyst is selected from the group consisting of: [NH$_4$] TFA, [NH$_4$]Cl, [NH$_4$]$_2$[SO$_4$], [NH$_4$]Br, Al(OTf)$_3$, Sc(OTf)$_3$, AlCl$_3$, AlBr$_3$, BR$_3$, BCl$_3$, BBr$_3$, BF$_3$, and Al(NO$_3$)$_3$.

11. The method according to claim 1, wherein the catalyst K is a ruthenium catalyst having the following formula IV:

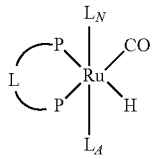
(IV)

where
P-L-P is the bidentate phosphane ligand of the formula (III) defined above;

$L_N$ is a neutral ligand selected from amines, phosphines, phosphites, alcohols, N-heterocyclic carbenes, imines, carbonyl compounds, olefines, alkynes or nitriles, and $L_A$ is absent or is an anionic ligand selected from chloride, fluoride, bromide, iodide, hydride, cyanide, alkoxy, amido or hydroxyl.

12. The method according to claim 1, wherein the amination is carried out enantioselectively by using a catalyst K bearing at least one chiral bidentate phosphane ligand according to formula III above.

13. The method according to claim 1, wherein the carbonyl compound to be aminated is a compound of the following formula II,

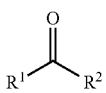

where $R^1$ and $R^2$ are the same or different and are mutually independently selected from the group consisting of:
H,
optionally mono- or polysubstituted alkyl, wherein the carbon chain is optionally interrupted by one or more carbonyl groups,
optionally mono- or polysubstituted cycloalkyl, wherein the carbocyclic ring is optionally interrupted by one or more carbonyl groups,
optionally mono- or polysubstituted heterocyclyl, wherein the heterocyclic ring is optionally interrupted by one or more carbonyl groups,
optionally mono- or polysubstituted aryl and
optionally mono- or polysubstituted hetaryl;
where the substituents optionally present are selected from the group consisting of halogen, —OH, —CN, —NH$_2$, $C_1$-$C_{30}$-alkyl, $C_3$-$C_{30}$-cycloalkyl, $C_3$-$C_{30}$-heterocyclyl, $C_5$-$C_{14}$-aryl, $C_5$-$C_{14}$-heteroaryl, —OR$_7$, —NHR$_7$ or —N(R$_7$)$_2$, —C(O)R$_7$, —C(O)OR$_7$, —C(O)NHR$_7$ and —C(O)N(R$_7$)$_2$, where R$_7$ is selected from the group consisting of $C_1$-$C_{30}$-alkyl and $C_5$-$C_{30}$-aryl.

14. The method according to claim 1, wherein the catalyst K is formed from a catalyst precursor selected from the following compounds:
[Ru(PPh$_3$)$_3$(H)(Cl)(CO)], [Ru(PPh$_3$)$_3$(H)$_2$(CO)], [Ru(PPh$_3$)$_3$(Cl)$_2$], [Ru(PPh3)$_3$(Cl)$_2$(CO)], [Ru(p-cymene)(Cl)$_2$], [Ru(benzene)Cl$_2$]$_n$, [Ru(CO)$_2$Cp]$_n$ [Ru(CO)$_3$(Cl)$_2$][Ru(COD)(allyl)], [Ru(COD)(2-methylallyl)$_2$], [RuCl3*H$_2$O], [Ru(acetylacetonate)$_3$], [Ru(DMSO)$_4$(Cl)$_2$], Ru$_3$CO$_{12}$,[Ru(cyclopentadienyl)(PPh$_3$)$_2$(Cl)], Ru(cyclopentadienyl)(CO)$_2$(Cl)], [Ru(cyclopentadienyl)(CO)$_2$H], [Ru(cyclopentadienyl)(CO)$_2$]$_2$, [Ru(pentamethylcyclopentadienyl)(CO)$_2$(Cl)], [Ru(pentamethylcylcopentadienyl)(CO)$_2$H], [Ru(pentamethylcyclopentadienyl)(CO)$_2$]$_2$, [Ru(indenyl)(CO)$_2$(Cl)], [Ru(indenyl)(CO)$_2$(H)], [Ru(indenyl)(CO)$_2$]$_2$, ruthenocene, [Ru(binap)Cl$_2$], [Ru(bipyridine)$_2$ Cl$_2$*2H$_2$O], [Ru(COD)Cl$_2$]$_2$, [Ru(pentamethylcyclopentadienyl)(COD)(Cl)], [Ru$_3$(CO)$_{12}$], [Ru(tetraphenylhydroxycyclopentadienyl)(CO)$_2$(H)], [Ru(PPh$_3$)$_4$ (H)$_2$].

15. The method according to claim 1, wherein the catalyst K is used in an amount of 1 to 5000 ppm by weight, based on the total weight of the liquid reaction medium used.

16. The method according to claim 1, wherein the reaction is carried out under the following reaction conditions:

a) temperature in the range of 20 to 250° C. and/or
b) total pressure in the range of 0.1 to 30 MPa and/or
c) reaction time of 0.1 to 100 h and/or
d) ammonia: 1.5 to 250-fold molar excess, based on the moles of reactant used and/or
e) 1.5 to 250-fold molar excess of hydrogen based on the moles of reactant used.

* * * * *